(12) United States Patent
Woo et al.

(10) Patent No.: US 9,441,230 B2
(45) Date of Patent: Sep. 13, 2016

(54) **SHUTTLE VECTOR FOR *CORYNEBACTERIUM* OR *E. COLI***

(71) Applicant: KOREA INSTITUTE OF SCIENCE AND TECHNOLOGY, Seoul (KR)

(72) Inventors: Han Min Woo, Seoul (KR); Youngsoon Um, Seoul (KR); Yunje Kim, Seoul (KR); Gyeong Taek Gong, Seoul (KR); Jung Seok Lee, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 14/637,355

(22) Filed: Mar. 3, 2015

(65) Prior Publication Data
US 2016/0115491 A1    Apr. 28, 2016

(30) Foreign Application Priority Data
Oct. 27, 2014 (KR) .................. 10-2014-0146255

(51) Int. Cl.
*C12N 15/77* (2006.01)
*C12N 15/72* (2006.01)

(52) U.S. Cl.
CPC ............. *C12N 15/77* (2013.01); *C12N 15/72* (2013.01)

(58) Field of Classification Search
None
See application file for complete search history.

(56) References Cited

U.S. PATENT DOCUMENTS

| 4,992,371 A | 2/1991 | Wohlleben et al. |
| 2012/0259607 A1 | 10/2012 | Hillson et al. |

FOREIGN PATENT DOCUMENTS

| JP | 2619855 B2 | 3/1997 |
| KR | 101039596 B1 | 6/2011 |
| KR | 101213179 B1 | 12/2012 |
| KR | 20140042398 A | 4/2014 |

OTHER PUBLICATIONS

Jakoby et al., Construction and application of new Corynebacterium glutamicum vectors,Biotechnology Techniques ,1999., pp. 437-441, vol. 13, Netherlands.
Lee et al. BglBrick vectors and datasheets: A synthetic biology platform for gene expression,Journal of Biological Engineering, 2011, vol. 5, No. 12.
Quan et al., Circular Polymerase Extension Cloning of Complex Gene Libraries and Pathways, PLoS One, 2009 , vol. 4, No. 7.
Javed Equbal et al.,Novel expression system for Corynebacterium acetoacidophilum and *Escherichia coli* based on the T7 RNA polymerase-dependent promoter, Applied Microbiology and Biotechnology, Apr. 28, 2013, pp. 7755-7766, vol. 97.

*Primary Examiner* — Jim Ketter
(74) *Attorney, Agent, or Firm* — Goldilocks Zone IP Law

(57) ABSTRACT

Disclosed is a shuttle vector that can be used for *Corynebacterium* and *E. coli*, containing: a repressor selected from a group consisting of a lacI repressor and a tetR repressor; a promoter selected from a group consisting of a trc promoter, a tetA promoter and a LacUV5 promoter; a replication origin pBL1 derived from *Corynebacterium glutamicum*; and a replication origin ColE1 of *E. coli*. A host cell transformed with the shuttle vector can effectively produce industrially useful substances. Also, the shuttle vector may be used to easily insert various combinations of target genes and, as a result, a variety of vectors can be prepared effectively.

20 Claims, 14 Drawing Sheets

Fig. 9a

GACGTCGACACCATCGAATGGTGCAAAACCTTTCGCGGTATGGCATGATAGCGCCCGGAAGAGAGTCAAT
TCAGGGTGGTGAATGTGAAACCAGTAACGTTATACGATGTCGCAGAGTATGCCGGTGTCTCTTATCAG
ACCGTTTCCCGCGTGGTGAACCAGGCCAGCCACGTTTCTGCGAAAACGCGGGAAAAAGTGGAAGC
GGCGATGGCGGAGCTGAATTACATTCCCAACCGCGTGGCACAACAACTGGCGGGCAAACAGTCGTT
GCTGATTGGCGTTGCCACCTCCAGTCTGGCCCTGCACGCGCCGTCGCAAATTGTCGCGGCGATTAAAT
CTCGCGCCGATCAACTGGGTGCCAGCGTGGTGGTGTCGATGGTAGAACGAAGCGGCGTCGAAGCCT
GTAAAGCGGCGGTGCACAATCTTCTCGCGCAACGCGTCAGTGGGCTGATCATTAACTATCCGCTGGA
TGACCAGGATGCCATTGCTGTGGAAGCTGCCTGCACTAATGTTCCGGCGTTATTTCTTGATGTCTCTG
ACCAGACACCCATCAACAGTATTATTTTCTCCCATGAAGACGGTACGCGACTGGGCGTGGAGCATCT
GGTCGCATTGGGTCACCAGCAAATCGCGCTGTTAGCGGGCCCATTAAGTTCTGTCTCGGCGCGTCTG
CGTCTGGCTGGCTGGCATAAATATCTCACTCGCAATCAAATTCAGCCGATAGCGGAACGGGAAGGCG
ACTGGAGTGCCATGTCCGGTTTTCAACAAACCATGCAAATGCTGAATGAGGGCATCGTTCCCACTGC
GATGCTGGTTGCCAACGATCAGATGGCGCTGGGCGCAATGCGCGCCATTACCGAGTCCGGGCTGCGC
GTTGGTGCGGATATCTCGGTAGTGGGATACGACGATACCGAAGACAGCTCATGTTATATCCCGCCGTT
AACCACCATCAAACAGGATTTTCGCCTGCTGGGGCAAACCAGCGTGGACCGCTTGCTGCAACTCTCT
CAGGGCCAGGCGGTGAAGGGCAATCAGCTGTTGCCCGTCTCACTGGTGAAAAGAAAAACCACCCTG
GCGCCCAATACGCAAACCGCCTCTCCCCGCGCGTTGGCCGATTCATTAATGCAGCTGGCACGACAGG
TTTCCCGACTGGAAAGCGGGCAGTGAGCGCAACGCAATTAATGTAAGTTAGCGCGAATTGATCTGGTTT
GACAGCTTATCATCGACTGCACGGTGCACCAATGCTTCTGGCGTCAGGCAGCCATCGGAAGCTGTGGT
ATGGCTGTGCAGGTCGTAAATCACTGCATAATTCGTGTCGCTCAAGGCGCACTCCCGTTCTGGATAAT
GTTTTTTGCGCCGACATCATAACGGTTCTGGCAAATATTCTGAAATGAGCTGTTGACAATTAATCATC
CGGCTCGTATAATGTGTGGAATTGTGAGCGGATAACAATTTCAGAATTCAAAAGATCTTTTAAGAAGG
AGATATACATATGGCGAGTAGCGAAGACGTTATCAAAGAGTTCATGCGTTTCAAAGTTCGTATGGAAGGTT
CCGTTAACGGTCACGAGTTCGAAATCGAAGGTGAAGGTGAAGGTCGTCCGTACGAAGGTACCCAGACCG
CTAAACTGAAAGTTACCAAAGGTGGTCCGCTGCCGTTCGCTTGGGACATCCTGTCCCCGCAGTTCCAGTAC
GGTTCCAAAGCTTACGTTAAACACCCGGCTGACATCCCGGACTACCTGAAACTGTCCTTCCCGGAAGGTTT
CAAATGGGAACGTGTTATGAACTTCGAAGACGGTGGTGTTGTTACCGTTACCCAGGACTCCTCCCTGCAAG
ACGGTGAGTTCATCTACAAAGTTAAACTGCGTGGTACCAACTTCCCGTCCGACGGTCCGGTTATGCAGAAA
AAAACCATGGGTTGGGAAGCTTCCACCGAACGTATGTACCCGGAAGACGGTGCTCTGAAAGGTGAAATC
AAAATGCGTCTGAAACTGAAAGACGGTGGTCACTACGACGCTGAAGTTAAAACCACCTACATGGCTAAAA
AACCGGTTCAGCTGCCGGGTGCTTACAAAACCGACATCAAACTGGACATCACCTCCCACAACGAAGACTA
CACCATCGTTGAACAGTACGAACGTGCTGAAGGTCGTCACTCCACCGGTGCTTAAGGATCCAAACTCGAG
TAAGGATCTCCAGGCATCAAATAAAACGAAAGGCTCAGTCGAAAGACTGGGCCTTTCGTTTTATCTGTTGT
TTGTCGGTGAACGCTCTCTACTAGAGTCACACTGGCTCACCTTCGGGTGGGCCTTTCTGCGTTTATACCTAG
GGCGTTCGGCTGCGGCGAGCGGTATCAGCAGTTATTGGTGCCCTTCGAAATGACCGACCAAGCGACGCC
CAACCTGCCATCACGAGATTTCGATTCCACCGCCGCCTTCTATGAAAGGTTGGGCTTCGGAATCGTTTTCC
GGGACGCCAACAACAAGACCCATCATAGTTTGCCCCCGCGACATTGACCATAAATTCATCGCACAAA
ATATCGAACGGGGTTTATGCCGCTTTTAGTGGGTGCGAAGAATAGTCTGCTCATTACCCGCGAACACC
GCCGCATTCAGATCACGCTTAGTAGCGTCCCCATGAGTAGGCAGAACCGCGTCCAAGTCCACATCATC
CATAACGATCATGCACGGGGTGGAATCCACACCCAGACTTGCCAGCACCTCATTAGCGACACGTTGC
GCAGCGGCCACGTCCTTAGCCTTATCCACGCAATCGAGAACGTACTGCCTAACCGCGAAATCAGACT
GAATCAGTTTCCAATCATCGGGCTTCACCAAAGCAACAGCAACGCGGGTTGATTCGACCCGTTCCGG
TGCTTCCAGACCGGCGAGCTTGTACAGTTCTTCTTCCATTTCACGACGTACATCAGCGTCTATGTAATC
AATGCCCAAAGCACGCTTAGCCCCACGTGACCAGGACGAACGCAGGTTTTTAGAACCAACCTCATA
CTCACGCCACCGAGCCACCAAAACAGCGTCCATATCCTCGCCGGCGTCGCTTTGATCGGCCAACATAT
CCAACATCTGAAACGGCGTGTACGACCCCTTAGACGCGGTTTTAGTAGCGGAGCCAGTCAGTTCCTG
AGACATGCCCTTAGCGAGGTAGGTTGCCATTTTCGCAGCGTCTCCACCCCAGGTAGACACCTGATCA
AGTTTGACCCCGTGCTCACGCAGTGGCGCGTCCATACCGGCCTTAACCACACCAGCAGACCAGCGGG
AAAACATGGAATCCTCAAACGCCTTGAGTTCATCGTCAGACAGTGGACGATCCAAGAACAACAGCA
TGTTGCGGTGCAAGTGCCAACCGTTCGCCCAAGAGTCTGTGACCTCATAGTCACTATAGGTGTGCTCC

Fig. 9b

ACCCCGTACCGTGCACGTTCTTTCTTCCACTGAGATGTTTTCACCATCGAAGAGTACGCAGTCTTAATA
CCCGCTTCAACCTGCGCAAATGACTGTGAGCGGTTGTGTCGAACAGTGCCCACAAACATCATGAGCG
CGCCACCCGCCGCCAAGTGATTCTTAGTAGCAATAGCCAGCTCAATGCGGCGTTCGCCCATGACTTCC
AATTCAGCCAGAGGTGACCCCCAGCGAGAGTGAGAGTTTTGCAGACCCTCAAACTGCGAAGCACCG
TTAGACGACCAGGACACCGCAACAGCTTCGTCCCTGCGCCACCTATGGCACCCCGCCAGAGCCTTAC
TATTGGTGATCTTGTACATGACGTTTTGCCTACGCCACGCCCTAGCGCGAGTGACCTTAGAACCCTCA
TTGACCTGCGGTTCCTTAGAGGTGTTCACTTCTATTTCAGTGTTACTCAGTGTTACCTAGACCCGATGT
TGTGCGGGGTTGCGCAGTGCGAGTTTGTGCGGGTGTTGTGCCCGTTGTCTTAGCTAGTGCTATGGTTG
TCAATTGAAACCCCTTCGGGTTATGTGGCCCCCGTGCATATGAGTTGGTAGCTCGCACGGGGGTTTGT
CTTGTCTAGGGACTATTAATTTTTAGTGGTGTTTGGTGGCCGCCTAGCTTGGCTATGCGTGCCAGCTT
ACCCGTACTCAATGTTAAAGATTTGCATCGACATGGGAGGGTTACGTGTCCGATACCTAGGGGGGGT
ATCCGCGACTAGGTGCCCCGGTGCTCACTGTCTGTACCGGCGGGGCAAGCCCCACACCCCGCATGGA
CAGGGTGGCTCCGCCCCCTGCACCCCCAGCAATCTGCATGTACATGTTTTACACATTAGCACGACATG
ACTGCATGTGCATGCACTGCATGCAGACTAGGTAAATATGAGTATGTACGACTAGTAACAGGAGCAC
TGCACATAATGAATGAGTTGCAGGACAATGTTTGCTACGCATGCGCATGACATATCGCAGGAAAGCT
ACTAGAGTCTTAAAGCATGGCAACCAAGGCACAGCTAGAACAGCAACTACAAGAAGCTCAACAGG
CACTACAGGCGCAGCAAGCGCAGGCACAAGCCACCATCGAAGCACTAGAAGCGCAGGCAAAGGCT
AAGCCCGTCGTGGTCACCGCACGCGTTCCTTTGGCACTACGTGAGGACATGAAGCGCGCAGGCATG
CAGAACGGTGAAAACCTCCAAGAGTTCATGATCGCCGCGTTTACCGAGCGGCTAGAAAAGCTCACC
ACCACCGACAACGAGGAAAACAATGTCTAACCCACTAGTTCTCTTTGCCCACCGTGACCCGGTAAAT
GACGTGACGTTCGAGTGCATTGAGCACGCCACCTACGACACACTTTCACACGCTAAAGACCAGATCA
CCGCCCAAATGCAAGCCCTAGACGAAGAAGCCGCCCTACTGCCCTAATGGGTGTTTCATGGGTGTTT
CCCTAGTGTTTCATGGTGTTTTCACCTAAGCTAGGGAATTGCGCGAGAAGTCTCGCAAAAATCAGCA
ACCCCCGGAACCACACAGTTCACGGGGGTTCTTCTATGCCAGAAATCAGAAAGGGGAACCAGTGAA
CGACCCCGAATGGCTGGATGATCCTCCAGCGCGGGGATCTCATGCTGGAGTTCTTCGCCCACCCCAAAAG
GATCTAGGTGAAGATCCTTTTTGATAATCTCATGACCAAAATCCCTTAACGTGAGTTTTCGTTCCACTGAGC
GTCAGACCCCGTATGAGCAAAAGGCCAGCAAAAGGCCAGGAACCGTAAAAAGGCCGCGTTGCTGGCGT
TTTTCCATAGGCTCCGCCCCCCTGACGAGCATCACAAAAATCGACGCTCAAGTCAGAGGTGGCGAAACCC
GACAGGACTATAAAGATACCAGGCGTTTCCCCCTGGAAGCTCCCTCGTGCGCTCTCCTGTTCCGACCCTGC
CGCTTACCGGATACCTGTCCGCCTTTCTCCCTTCGGGAAGCGTGGCGCTTTCTCATAGCTCACGCTGTAGGT
ATCTCAGTTCGGTGTAGGTCGTTCGCTCCAAGCTGGGCTGTGTGCACGAACCCCCCGTTCAGCCCGACCGC
TGCGCCTTATCCGGTAACTATCGTCTTGAGTCCAACCCGGTAAGACACGACTTATCGCCACTGGCAGCAGC
CACTGGTAACAGGATTAGCAGAGCGAGGTATGTAGGCGGTGCTACAGAGTTCTTGAAGTGGTGGCCTAAC
TACGGCTACACTAGAAGGACAGTATTTGGTATCTGCGCTCTGCTGAAGCCAGTTACCTTCGGAAAAAGAG
TTGGTAGCTCTTGATCCGGCAAACAAACCACCGCTGGTAGCGGTGGTTTTTTTGTTTGCAAGCAGCAGATT
ACGCGCAGAAAAAAAGGATCTCAAGAAGATCCTTTGATCTTTTCTACGGGGTCTGACGCTCAGTGGAACG
AAAACTCACGTTAAGGGATTTTGGTCATGACTAGTGCTTGGATTCTCACCAATAAAAAACGCCCGGCGGC
AACCGAGCGTTCTGAACAAATCCAGATGGAGTTCTGAGGTCATTACTGGATCTATCAACAGGAGTCCAAG
CGAGCTCGATATCAAATTACGCCCCGCCCTGCCACTCATCGCAGTACTGTTGTAATTCATTAAGCATTCTGC
CGACATGGAAGCCATCACAAACGGCATGATGAACCTGAATCGCCAGCGGCATCAGCACCTTGTCGCCTTG
CGTATAATATTTGCCCATGGTGAAAACGGGGGCGAAGAAGTTGTCCATATTGGCCACGTTTAAATCAAAAC
TGGTGAAACTCACCCAGGGATTGGCTGAGACGAAAAACATATTCTCAATAAACCCTTTAGGGAAATAGGC
CAGGTTTTCACCGTAACACGCCACATCTTGCGAATATATGTGTAGAAACTGCCGGAAATCGTCGTGGTATTC
ACTCCAGAGCGATGAAAACGTTTCAGTTTGCTCATGGAAAACGGTGTAACAAGGGTGAACACTATCCCAT
ATCACCAGCTCACCGTCTTTCATTGCCATACGAAATTCCGGATGAGCATTCATCAGGCGGGCAAGAATGTG
AATAAAGGCCGGATAAAACTTGTGCTTATTTTCTTTACGGTCTTTAAAAAGGCCGTAATATCCAGCTGAAC
GGTCTGGTTATAGGTACATTGAGCAACTGACTGAAATGCCTCAAAATGTTCTTTACGATGCCATTGGGATAT
ATCAACGGTGGTATATCCAGTGATTTTTTTCTCCATTTAGCTTCCTTAGCTCCTGAAAATCTCGATAACTCA
AAAAATACGCCCGGTAGTGATCTTATTTCATTATGGTGAAAGTTGGAACCTCTTACGTGCCGATCAACGTCT
CATTTTCGCCAGATATC

Fig. 10a

GACGTCTTAAGACCCACTTT**CACATTTAAGTTGTTTTTCTAATCCGCATATGATCAATTCAAGGCCGAAT
AAGAAGGCTGGCTCTGCACCTTGGTGATCAAATAATTCGATAGCTTGTCGTAATAATGGCGGCATACT
ATCAGTAGTAGGTGTTTCCCTTTCTTCTTTAGCGACTTGATGCTCTTGATCTTCCAATACGCAACCTAA
AGTAAAATGCCCCACAGCGCTGAGTGCATATAATGCATTCTCTAGTGAAAAACCTTGTTGGCATAAA
AAGGCTAATTGATTTTCGAGAGTTTCATACTGTTTTTCTGTAGGCCGTGTACCTAAATGTACTTTTGCT
CCATCGCGATGACTTAGTAAAGCACATCTAAAACTTTTAGCGTTATTACGTAAAAAATCTTGCCAGCT
TTCCCCTTCTAAAGGGCAAAAGTGAGTATGGTGCCTATCTAACATCTCAATGGCTAAGGCGTCGAGC
AAAGCCCGCTTATTTTTTACATGCCAATACAATGTAGGCTGCTCTACACCTAGCTTCTGGGCGAGTTT
ACGGGTTGTTAAACCTTCGATTCCGACCTCATTAAGCAGCTCTAATGCGCTGTTAATCACTTTACTTTT
ATCTAATCTAGACATCATTAATTCCTAATTTTTGTTGACACTCTATCGTTGATAGAGTTATTTTACCACTCC
CTATCAGTGATAGAGAAAAGAATTC**AAAAGATCTTTTAAGAAGGAGATATACATATGGCGAGTAGCGAA
GACGTTATCAAAGAGTTCATGCGTTTCAAAGTTCGTATGGAAGGTTCCGTTAACGGTCACGAGTTCGAAAT
CGAAGGTGAAGGTGAAGGTCGTCCGTACGAAGGTACCCAGACCGCTAAACTGAAAGTTACCAAAGGTGG
TCCGCTGCCGTTCGCTTGGGACATCCTGTCCCCGCAGTTCCAGTACGGTTCCAAAGCTTACGTTAAACACC
CGGCTGACATCCCGGACTACCTGAAACTGTCCTTCCCGGAAGGTTTCAAATGGGAACGTGTTATGAACTTC
GAAGACGGTGGTGTTGTTACCGTTACCCAGGACTCCTCCCTGCAAGACGGTGAGTTCATCTACAAAGTTAA
ACTGCGTGGTACCAACTTCCCGTCCGACGGTCCGGTTATGCAGAAAAAAACCATGGGTTGGGAAGCTTCC
ACCGAACGTATGTACCCGGAAGACGGTGCTCTGAAAGGTGAAATCAAAATGCGTCTGAAACTGAAAGAC
GGTGGTCACTACGACGCTGAAGTTAAAACCACCTACATGGCTAAAAAACCGGTTCAGCTGCCGGGTGCTT
ACAAAACCGACATCAAACTGGACATCACCTCCCACAACGAAGACTACACCATCGTTGAACAGTACGAACG
TGCTGAAGGTCGTCACTCCACCGGTGCTTAAGGATCCAAACTCGAGTAAGGATCTCCAGGCATCAAATAA
AACGAAAGGCTCAGTCGAAAGACTGGGCCTTTCGTTTTATCTGTTGTTTGTCGGTGAACGCTCTCTACTAG
AGTCACACTGGCTCACCTTCGGGTGGGCCTTTCTGCGTTTATACCTAGGGCGTTCGGCTGCGGCGAGCGG
TATCAGCAGTTATTGGTGCCCTTCGAAATGACCGACCAAGCGACGCCCAACCTGCCATCACGAGATTTCGA
TTCCACCGCCGCCTTCTATGAAAGGTTGGGCTTCGGAATCGTTTTCCGGGACGCC**AACAACAAGACCCAT
CATAGTTTGCCCCCGCGACATTGACCATAAATTCATCGCACAAAATATCGAACGGGGTTTATGCCGCT
TTTAGTGGGTGCGAAGAATAGTCTGCTCATTACCCGCGAACACCGCCGCATTCAGATCACGCTTAGTA
GCGTCCCCATGAGTAGGCAGAACCGCGTCCAAGTCCACATCATCCATAACGATCATGCACGGGGTGG
AATCCACACCCAGACTTGCCAGCACCTCATTAGCGACACGTTGCGCAGCGGCCACGTCCTTAGCCTT
ATCCACGCAATCGAGAACGTACTGCCTAACCGCGAAATCAGACTGAATCAGTTTCCAATCATCGGGC
TTCACCAAAGCAACAGCAACGCGGGTTGATTCGACCCGTTCCGGTGCTTCCAGACCGGCGAGCTTGT
ACAGTTCTTCTTCCATTTCACGACGTACATCAGCGTCTATGTAATCAATGCCCAAAGCACGCTTAGCCC
CACGTGACCAGGACGAACGCAGGTTTTTAGAACCAACCTCATACTCACGCCACCGAGCCACCAAAA
CAGCGTCCATATCCTCGCCGGCGTCGCTTTGATCGGCCAACATATCCAACATCTGAAACGGCGTGTAC
GACCCCTTAGACGCGGTTTTAGTAGCGGAGCCAGTCAGTTCCTGAGACATGCCCTTAGCGAGGTAGG
TTGCCATTTTCGCAGCGTCTCCACCCCAGGTAGACACCTGATCAAGTTTGACCCCGTGCTCACGCAGT
GGCGCGTCCATACCGGCCTTAACCACACCAGCAGACCAGCGGGAAAACATGGAATCCTCAAACGCC
TTGAGTTCATCGTCAGACAGTGGACGATCCAAGAACAACAGCATGTTGCGGTGCAAGTGCCAACCG
TTCGCCCAAGAGTCTGTGACCTCATAGTCACTATAGGTGTGCTCCACCCCGTACCGTGCACGTTCTTTC
TTCCACTGAGATGTTTTCACCATCGAAGAGTACGCAGTCTTAATACCCGCTTCAACCTGCGCAAATGA
CTGTGAGCGGTTGTGTCGAACAGTGCCCACAAACATCATGAGCGCGCCACCCGCCGCCAAGTGATTC
TTAGTAGCAATAGCCAGCTCAATGCGGCGTTCGCCCATGACTTCCAATTCAGCCAGAGGTGACCCCC
AGCGAGAGTGAGAGTTTTGCAGACCCTCAAACTGCAAGCACCGTTAGACGACCAGGACACCGCA
ACAGCTTCGTCCCTGCGCCACCTATGGCACCCCGCCAGAGCCTTACTATTGGTGATCTTGTACATGAC
GTTTTGCCTACGCCACGCCCTAGCGCGAGTGACCTTAGAACCCTCATTGACCTGCGGTTCCTTAGAGG
TGTTCACTTCTATTTCAGTGTTACTCAGTGTTACCTAGACCCGATGTTGTGCGGGGTTGCGCAGTGCG
AGTTTGTGCGGGTGTTGTGCCCGTTGTCTTAGCTAGTGCTATGGTTGTCAATTGAAACCCCTTCGGGT
TATGTGGCCCCCGTGCATATGAGTTGGTAGCTCGCACGGGGGTTTGTCTTGTCTAGGGACTATTAATT**

Fig. 10b

TTTAGTGGTGTTTGGTGGCCGCCTAGCTTGGCTATGCGTGCCAGCTTACCCGTACTCAATGTTAAAGA
TTTGCATCGACATGGGAGGGTTACGTGTCCGATACCTAGGGGGGGTATCCGCGACTAGGTGCCCCGG
TGCTCACTGTCTGTACCGGCGGGGCAAGCCCCACACCCCGCATGGACAGGGTGGCTCCGCCCCCTGC
ACCCCCAGCAATCTGCATGTACATGTTTTACACATTAGCACGACATGACTGCATGTGCATGCACTGCA
TGCAGACTAGGTAAATATGAGTATGTACGACTAGTAACAGGAGCACTGCACATAATGAATGAGTTGC
AGGACAATGTTTGCTACGCATGCGCATGACATATCGCAGGAAAGCTACTAGAGTCTTAAAGCATGGC
AACCAAGGCACAGCTAGAACAGCAACTACAAGAAGCTCAACAGGCACTACAGGCGCAGCAAGCG
CAGGCACAAGCCACCATCGAAGCACTAGAAGCGCAGGCAAAGGCTAAGCCCGTCGTGGTCACCGC
ACGCGTTCCTTTGGCACTACGTGAGGACATGAAGCGCGCAGGCATGCAGAACGGTGAAAACCTCCA
AGAGTTCATGATCGCCGCGTTTACCGAGCGGCTAGAAAAGCTCACCACCACCGACAACGAGGAAAA
CAATGTCTAACCCACTAGTTCTCTTTGCCCACCGTGACCCGGTAAATGACGTGACGTTCGAGTGCATT
GAGCACGCCACCTACGACACACTTTCACACGCTAAAGACCAGATCACCGCCCAAATGCAAGCCCTA
GACGAAGAAGCCGCCCTACTGCCCTAATGGGTGTTTCATGGGTGTTTCCCTAGTGTTTCATGGTGTTT
TCACCTAAGCTAGGGAATTGCGCGAGAAGTCTCGCAAAAATCAGCAACCCCCGGAACCACACAGTT
CACGGGGGTTCTTCTATGCCAGAAATCAGAAAGGGGAACCAGTGAACGACCCCGAATGGCTGGATG
ATCCTCCAGCGCGGGGATCTCATGCTGGAGTTCTTCGCCCACCCCAAAAGGATCTAGGTGAAGATCCTTTT
TGATAATCTCATGACCAAAATCCCTTAACGTGAGTTTTCGTTCCACTGAGCGTCAGACCCCGTATGAGCAAA
AGGCCAGCAAAAGGCCAGGAACCGTAAAAAGGCCGCGTTGCTGGCGTTTTTCCATAGGCTCCGCCCCCC
TGACGAGCATCACAAAAATCGACGCTCAAGTCAGAGGTGGCGAAACCCGACAGGACTATAAAGATACCA
GGCGTTTCCCCCTGGAAGCTCCCTCGTGCGCTCTCCTGTTCCGACCCTGCCGCTTACCGGATACCTGTCCG
CCTTTCTCCCTTCGGGAAGCGTGGCGCTTTCTCATAGCTCACGCTGTAGGTATCTCAGTTCGGTGTAGGTCG
TTCGCTCCAAGCTGGGCTGTGTGCACGAACCCCCCGTTCAGCCCGACCGCTGCGCCTTATCCGGTAACTAT
CGTCTTGAGTCCAACCCGGTAAGACACGACTTATCGCCACTGGCAGCAGCCACTGGTAACAGGATTAGCA
GAGCGAGGTATGTAGGCGGTGCTACAGAGTTCTTGAAGTGGTGGCCTAACTACGGCTACACTAGAAGGAC
AGTATTTGGTATCTGCGCTCTGCTGAAGCCAGTTACCTTCGGAAAAAGAGTTGGTAGCTCTTGATCCGGCA
AACAAACCACCGCTGGTAGCGGTGGTTTTTTTGTTTGCAAGCAGCAGATTACGCGCAGAAAAAAAGGAT
CTCAAGAAGATCCTTTGATCTTTTCTACGGGGTCTGACGCTCAGTGGAACGAAAACTCACGTTAAGGGATT
TTGGTCATGACTAGTGCTTGGATTCTCACCAATAAAAAACGCCCGGCGGCAACCGAGCGTTCTGAACAAA
TCCAGATGGAGTTCTGAGGTCATTACTGGATCTATCAACAGGAGTCCAAGCGAGCTCGATATCAAATTACG
CCCCGCCCTGCCACTCATCGCAGTACTGTTGTAATTCATTAAGCATTCTGCCGACATGGAAGCCATCACAA
ACGGCATGATGAACCTGAATCGCCAGCGGCATCAGCACCTTGTCGCCTTGCGTATAATATTTGCCCATGGT
GAAAACGGGGGCGAAGAAGTTGTCCATATTGGCCACGTTTAAATCAAAACTGGTGAAACTCACCCAGGG
ATTGGCTGAGACGAAAAACATATTCTCAATAAACCCTTTAGGGAAATAGGCCAGGTTTTCACCGTAACACG
CCACATCTTGCGAATATATGTGTAGAAACTGCCGGAAATCGTCGTGGTATTCACTCCAGAGCGATGAAAAC
GTTTCAGTTTGCTCATGGAAAACGGTGTAACAAGGGTGAACACTATCCCATATCACCAGCTCACCGTCTTT
CATTGCCATACGAAATTCCGGATGAGCATTCATCAGGCGGGCAAGAATGTGAATAAAGGCCGGATAAAAC
TTGTGCTTATTTTTCTTTACGGTCTTTAAAAAGGCCGTAATATCCAGCTGAACGGTCTGGTTATAGGTACATT
GAGCAACTGACTGAAATGCCTCAAAATGTTCTTTACGATGCCATTGGGATATATCAACGGTGGTATATCCAG
TGATTTTTTTCTCCATTTTAGCTTCCTTAGCTCCTGAAAATCTCGATAACTCAAAAAATACGCCCGGTAGTGA
TCTTATTTCATTATGGTGAAAGTTGGAACCTCTTACGTGCCGATCAACGTCTCATTTTCGCCAGATATC

Fig. 11a

GACGTCGGTGCCTAATGAGTGAGCTAACTTACATTAATTGCGTTGCGCTCACTGCCCGCTTTCCAGTCGG
GAAACCTGTCGTGCCAGCTGCATTAATGAATCGGCCAACGCGCGGGGAGAGGCGGTTTGCGTATTG
GGCGCCAGGGTGGTTTTTCTTTTCACCAGTGAGACGGGCAACAGCTGATTGCCCTTCACCGCCTGGC
CCTGAGAGAGTTGCAGCAAGCGGTCCACGCTGGTTTGCCCCAGCAGGCGAAAATCCTGTTTGATGG
TGGTTAACGGCGGGATATAACATGAGCTGTCTTCGGTATCGTCGTATCCCACTACCGAGATGTCCGCA
CCAACGCGCAGCCCGGACTCGGTAATGGCGCGCATTGCGCCCAGCGCCATCTGATCGTTGGCAACCA
GCATCGCAGTGGGAACGATGCCCTCATTCAGCATTTGCATGGTTTGTTGAAAACCGGACATGGCACT
CCAGTCGCCTTCCCGTTCCGCTATCGGCTGAATTTGATTGCGAGTGAGATATTTATGCCAGCCAGCCA
GACGCAGACGCGCCGAGACAGAACTTAATGGGCCCGCTAACAGCGCGATTTGCTGGTGACCCAATG
CGACCAGATGCTCCACGCCCAGTCGCGTACCGTCTTCATGGGAGAAAATAATACTGTTGATGGGTGTC
TGGTCAGAGACATCAAGAAATAACGCCGGAACATTAGTGCAGGCAGCTTCCACAGCAATGGCATCC
TGGTCATCCAGCGGATAGTTAATGATCAGCCCACTGACGCGTTGCGCGAGAAGATTGTGCACCGCCG
CTTTACAGGCTTCGACGCCGCTTCGTTCTACCATCGACACCACCACGCTGGCACCCAGTTGATCGGCG
CGAGATTTAATCGCCGCGACAATTTGCGACGGCGCGTGCAGGGCCAGACTGGAGGTGGCAACGCCA
ATCAGCAACGACTGTTTGCCCGCCAGTTGTTGTGCCACGCGGTTGGGAATGTAATTCAGCTCCGCCAT
CGCCGCTTCCACTTTTTCCCGCGTTTTCGCAGAAACGTGGCTGGCCTGGTTCACCACGCGGGAAACG
GTCTGATAAGAGACACCGGCATACTCTGCGACATCGTATAACGTTACTGGTTTCACATTCACCACCCT
GAATTGACTCTCTTCCGGGCGCTATCATGCCATACCGCGAAAGGTTTTGCGCCATTCGATGGTGTCCGGGA
TCTCGACGCTCTCCCTTATGCGACTCCTGCATTAGGAAGCAGCCCAGTAGTAGGTTGAGGCCGTTGAG
CACCGCCGCCGCAAGGAATGGTGCATGCAAGGAGATGGCGCCCAACAGTCCCCGGCCACGGGGCC
TGCCACCATACCCACGCCGAAACAAGCGCTCATGAGCCCGAAGTGGCGAGCCCGATCTTCCCCATCG
GTGATGTCGGCGATATAGGCGCCAGCAACCGCACCTGTGGCGCCGGTGATGCCGGCCACGATGCGTC
CGGCGTAGAGGATCGAGATCGTTTAGGCACCCCAGGCTTTACACTTTATGCTTCCGGCTCGTATAATG
TGTGGAATTGTGAGCGGATAACAATTTCAGAATTCAAAAGATCTTTTAAGAAGGAGATATACATATGGC
GAGTAGCGAAGACGTTATCAAAGAGTTCATGCGTTTCAAAGTTCGTATGGAAGGTTCCGTTAACGGTCACG
AGTTCGAAATCGAAGGTGAAGGTGAAGGTCGTCCGTACGAAGGTACCCAGACCGCTAAACTGAAAGTTAC
CAAAGGTGGTCCGCTGCCGTTCGCTTGGGACATCCTGTCCCCGCAGTTCCAGTACGGTTCCAAAGCTTACG
TTAAACACCCGGCTGACATCCCGGACTACCTGAAACTGTCCTTCCCGGAAGGTTTCAAATGGGAACGTGTT
ATGAACTTCGAAGACGGTGGTGTTGTTACCGTTACCCAGGACTCCTCCCTGCAAGACGGTGAGTTCATCTA
CAAAGTTAAACTGCGTGGTACCAACTTCCCGTCCGACGGTCCGGTTATGCAGAAAAAAACCATGGGTTGG
GAAGCTTCCACCGAACGTATGTACCCGGAAGACGGTGCTCTGAAAGGTGAAATCAAAATGCGTCTGAAAC
TGAAAGACGGTGGTCACTACGACGCTGAAGTTAAAACCACCTACATGGCTAAAAAACCGGTTCAGCTGCC
GGGTGCTTACAAAACCGACATCAAACTGGACATCACCTCCCACAACGAAGACTACACCATCGTTGAACAG
TACGAACGTGCTGAAGGTCGTCACTCCACCGGTGCTTAAGGATCCAAACTCGAGTAAGGATCTCCAGGCA
TCAAATAAAACGAAAGGCTCAGTCGAAAGACTGGGCCTTTCGTTTTATCTGTTGTTTGTCGGTGAACGCTC
TCTACTAGAGTCACACTGGCTCACCTTCGGGTGGGCCTTTCTGCGTTTATACCTAGGGCGTTCGGCTGCGG
CGAGCGGTATCAGCAGTTATTGGTGCCCTTCGAAATGACCGACCAAGCGACGCCCAACCTGCCATCACGA
GATTTCGATTCCACCGCCGCCTTCTATGAAAGGTTGGGCTTCGGAATCGTTTTCCGGGACGCCAACAACA
AGACCCATCATAGTTTGCCCCCGCGACATTGACCATAAATTCATCGCACAAAATATCGAACGGGGTTT
ATGCCGCTTTTAGTGGGTGCGAAGAATAGTCTGCTCATTACCCGCGAACACCGCCGCATTCAGATCAC
GCTTAGTAGCGTCCCCATGAGTAGGCAGAACCGCGTCCAAGTCCACATCATCCATAACGATCATGCAC
GGGGTGGAATCCACACCCAGACTTGCCAGCACCTCATTAGCGACACGTTGCGCAGCGGCCACGTCCT
TAGCCTTATCCACGCAATCGAGAACGTACTGCCTAACCGCGAAATCAGACTGAATCAGTTTCCAATCA
TCGGGCTTCACCAAAGCAACAGCAACGCGGGTTGATTCGACCCGTTCCGGTGCTTCCAGACCGGCG
AGCTTGTACAGTTCTTCTTCCATTTCACGACGTACATCAGCGTCTATGTAATCAATGCCCAAAGCACG
CTTAGCCCCACGTGACCAGGACGAACGCAGGTTTTTAGAACCAACCTCATACTCACGCCACCGAGCC
ACCAAAACAGCGTCCATATCCTCGCCGGCGTCGCTTTGATCGGCCAACATATCCAACATCTGAAACGG
CGTGTACGACCCCTTAGACGCGGTTTTAGTAGCGGAGCCAGTCAGTTCCTGAGACATGCCCTTAGCG
AGGTAGGTTGCCATTTTCGCAGCGTCTCCACCCCAGGTAGACACCTGATCAAGTTTGACCCCGTGCTC
ACGCAGTGGCGCGTCCATACCGGCCTTAACCACACCAGCAGACCAGCGGGAAAACATGGAATCCTC

Fig. 11b

AAACGCCTTGAGTTCATCGTCAGACAGTGGACGATCCAAGAACAACAGCATGTTGCGGTGCAAGTG
CCAACCGTTCGCCCAAGAGTCTGTGACCTCATAGTCACTATAGGTGTGCTCCACCCCGTACCGTGCAC
GTTCTTTCTTCCACTGAGATGTTTTCACCATCGAAGAGTACGCAGTCTTAATACCCGCTTCAACCTGC
GCAAATGACTGTGAGCGGTTGTGTCGAACAGTGCCCACAAACATCATGAGCGCGCCACCCGCCGCC
AAGTGATTCTTAGTAGCAATAGCCAGCTCAATGCGGCGTTCGCCCATGACTTCCAATTCAGCCAGAG
GTGACCCCCAGCGAGAGTGAGAGTTTTGCAGACCCTCAAACTGCGAAGCACCGTTAGACGACCAGG
ACACCGCAACAGCTTCGTCCCTGCGCCACCTATGGCACCCGCCAGAGCCTTACTATTGGTGATCTTG
TACATGACGTTTTGCCTACGCCACGCCCTAGCGCGAGTGACCTTAGAACCCTCATTGACCTGCGGTTC
CTTAGAGGTGTTCACTTCTATTTCAGTGTTACTCAGTGTTACCTAGACCCGATGTTGTGCGGGGTTGC
GCAGTGCGAGTTTGTGCGGGTGTTGTGCCCGTTGTCTTAGCTAGTGCTATGGTTGTCAATTGAAACCC
CTTCGGGTTATGTGGCCCCCGTGCATATGAGTTGGTAGCTCGCACGGGGGTTTGTCTTGTCTAGGGAC
TATTAATTTTTAGTGGTGTTTGGTGGCCGCCTAGCTTGGCTATGCGTGCCAGCTTACCCGTACTCAATG
TTAAAGATTTGCATCGACATGGGAGGGTTACGTGTCCGATACCTAGGGGGGGTATCCGCGACTAGGT
GCCCCGGTGCTCACTGTCTGTACCGGCGGGGCAAGCCCCACACCCCGCATGGACAGGGTGGCTCCGC
CCCCTGCACCCCCAGCAATCTGCATGTACATGTTTTACACATTAGCACGACATGACTGCATGTGCATG
CACTGCATGCAGACTAGGTAAATATGAGTATGTACGACTAGTAACAGGAGCACTGCACATAATGAAT
GAGTTGCAGGACAATGTTTGCTACGCATGCGCATGACATATCGCAGGAAAGCTACTAGAGTCTTAAA
GCATGGCAACCAAGGCACAGCTAGAACAGCAACTACAAGAAGCTCAACAGGCACTACAGGCGCAG
CAAGCGCAGGCACAAGCCACCATCGAAGCACTAGAAGCGCAGGCAAAGGCTAAGCCCGTCGTGGT
CACCGCACGCGTTCCTTTGGCACTACGTGAGGACATGAAGCGCGCAGGCATGCAGAACGGTGAAAA
CCTCCAAGAGTTCATGATCGCCGCGTTTACCGAGCGGCTAGAAAAGCTCACCACCACCGACAACGA
GGAAAACAATGTCTAACCCACTAGTTCTCTTTGCCCACCGTGACCCGGTAAATGACGTGACGTTCGA
GTGCATTGAGCACGCCACCTACGACACACTTTCACACGCTAAAGACCAGATCACCGCCCAAATGCAA
GCCCTAGACGAAGAAGCCGCCCTACTGCCCTAATGGGTGTTTCATGGGTGTTTCCCTAGTGTTTCATG
GTGTTTTCACCTAAGCTAGGGAATTGCGCGAGAAGTCTCGCAAAAATCAGCAACCCCCGGAACCAC
ACAGTTCACGGGGGTTCTTCTATGCCAGAAATCAGAAAGGGGAACCAGTGAACGACCCCGAATGGC
TGGATGATCCTCCAGCGCGGGGATCTCATGCTGGAGTTCTTCGCCCACCCCAAAAGGATCTAGGTGAAGAT
CCTTTTTGATAATCTCATGACCAAAATCCCTTAACGTGAGTTTTCGTTCCACTGAGCGTCAGACCCCGTATG
AGCAAAAGGCCAGCAAAAGGCCAGGAACCGTAAAAAGGCCGCGTTGCTGGCGTTTTTCCATAGGCTCC
GCCCCCCTGACGAGCATCACAAAAATCGACGCTCAAGTCAGAGGTGGCGAAACCCGACAGGACTATAAA
GATACCAGGCGTTTCCCCCTGGAAGCTCCCTCGTGCGCTCTCCTGTTCCGACCCTGCCGCTTACCGGATAC
CTGTCCGCCTTTCTCCCTTCGGGAAGCGTGGCGCTTTCTCATAGCTCACGCTGTAGGTATCTCAGTTCGGTG
TAGGTCGTTCGCTCCAAGCTGGGCTGTGTGCACGAACCCCCCGTTCAGCCCGACCGCTGCGCCTTATCCG
GTAACTATCGTCTTGAGTCCAACCCGGTAAGACACGACTTATCGCCACTGGCAGCAGCCACTGGTAACAG
GATTAGCAGAGCGAGGTATGTAGGCGGTGCTACAGAGTTCTTGAAGTGGTGGCCTAACTACGGCTACACT
AGAAGGACAGTATTTGGTATCTGCGCTCTGCTGAAGCCAGTTACCTTCGGAAAAAGAGTTGGTAGCTCTTG
ATCCGGCAAACAAACCACCGCTGGTAGCGGTGGTTTTTTTGTTTGCAAGCAGCAGATTACGCGCAGAAA
AAAAGGATCTCAAGAAGATCCTTTGATCTTTTCTACGGGGTCTGACGCTCAGTGGAACGAAAACTCACGTT
AAGGGATTTTGGTCATGACTAGTGCTTGGATTCTCACCAATAAAAAACGCCCGGCGGCAACCGAGCGTTC
TGAACAAATCCAGATGGAGTTCTGAGGTCATTACTGGATCTATCAACAGGAGTCCAAGCGAGCTCGATATC
AAATTACGCCCCGCCCTGCCACTCATCGCAGTACTGTTGTAATTCATTAAGCATTCTGCCGACATGGAAGCC
ATCACAAACGGCATGATGAACCTGAATCGCCAGCGGCATCAGCACCTTGTCGCCTTGCGTATAATATTTGC
CCATGGTGAAAACGGGGGCGAAGAAGTTGTCCATATTGGCCACGTTTAAATCAAAACTGGTGAAACTCAC
CCAGGGATTGGCTGAGACGAAAAACATATTCTCAATAAACCCTTTAGGGAAATAGGCCAGGTTTTCACCG
TAACACGCCACATCTTGCGAATATATGTGTAGAAACTGCCGGAAATCGTCGTGGTATTCACTCCAGAGCGAT
GAAAACGTTTCAGTTTGCTCATGGAAAACGGTGTAACAAGGGTGAACACTATCCCATATCACCAGCTCACC
GTCTTTCATTGCCATACGAAATTCCGGATGAGCATTCATCAGGCGGGCAAGAATGTGAATAAAGGCCGGAT
AAAACTTGTGCTTATTTTTCTTTACGGTCTTTAAAAAGGCCGTAATATCCAGCTGAACGGTCTGGTTATAGGT
ACATTGAGCAACTGACTGAAATGCCTCAAAATGTTCTTTACGATGCCATTGGGATATATCAACGGTGGTATA
TCCAGTGATTTTTTTCTCCATTTTAGCTTCCTTAGCTCCTGAAAATCTCGATAACTCAAAAAATACGCCCGGT
AGTGATCTTATTTCATTATGGTGAAAGTTGGAACCTCTTACGTGCCGATCAACGTCTCATTTTCGCCAGATAT
C

SEQUENCE LISTING

<160> NUMBER OF SEQ ID NOS: 4

<210> SEQ ID NO 1
<211> LENGTH: 6808
<212> TYPE: DNA
<213> ORGANISM: Artificial Sequence
<220> FEATURE:
<223> OTHER INFORMATION: pBbEB1c-RFP shuttle vector
<220> FEATURE:
<221> NAME/KEY: gene
<222> LOCATION: (76)..(1167)
<223> OTHER INFORMATION: lacI
<220> FEATURE:
<221> NAME/KEY: promoter
<222> LOCATION: (1224)..(1463)
<223> OTHER INFORMATION: pTrc
<220> FEATURE:
<221> NAME/KEY: promoter
<222> LOCATION: (2477)..(5031)
<223> OTHER INFORMATION: pBL1

<400> SEQUENCE: 1

| | | | | | |
|---|---|---|---|---|---|
| gacgtcgaca | ccatcgaatg | gtgcaaaacc | tttcgcggta | tggcatgata | gcgcccggaa | 60 |
| gagagtcaat | tcagggtggt | gaatgtgaaa | ccagtaacgt | tatacgatgt | cgcagagtat | 120 |
| gccggtgtct | cttatcagac | cgtttcccgc | gtggtgaacc | aggccagcca | cgtttctgcg | 180 |
| aaaacgcggg | aaaaagtgga | agcggcgatg | gcggagctga | attacattcc | caaccgcgtg | 240 |
| gcacaacaac | tggcgggcaa | acagtcgttg | ctgattggcg | ttgccacctc | cagtctggcc | 300 |
| ctgcacgcgc | cgtcgcaaat | tgtcgcggcg | attaaatctc | gcgccgatca | actgggtgcc | 360 |
| agcgtggtgg | tgtcgatggt | agaacgaagc | ggcgtcgaag | cctgtaaagc | ggcggtgcac | 420 |
| aatcttctcg | cgcaacgcgt | cagtgggctg | atcattaact | atccgctgga | tgaccaggat | 480 |
| gccattgctg | tggaagctgc | ctgcactaat | gttccggcgt | tatttcttga | tgtctctgac | 540 |
| cagacaccca | tcaacagtat | tattttctcc | catgaagacg | gtacgcgact | gggcgtggag | 600 |
| catctggtcg | cattgggtca | ccagcaaatc | gcgctgttag | cgggcccatt | aagttctgtc | 660 |
| tcggcgcgtc | tgcgtctggc | tggctggcat | aaatatctca | ctcgcaatca | aattcagccg | 720 |
| atagcggaac | gggaaggcga | ctggagtgcc | atgtccggtt | ttcaacaaac | catgcaaatg | 780 |
| ctgaatgagg | gcatcgttcc | cactgcgatg | ctggttgcca | acgatcagat | ggcgctgggc | 840 |
| gcaatgcgcg | ccattaccga | gtccgggctg | cgcgttggtg | cggatatctc | ggtagtggga | 900 |
| tacgacgata | ccgaagacag | ctcatgttat | atcccgccgt | taaccaccat | caaacaggat | 960 |
| tttcgcctgc | tggggcaaac | cagcgtggac | cgcttgctgc | aactctctca | gggccaggcg | 1020 |
| gtgaagggca | atcagctgtt | gcccgtctca | ctggtgaaaa | gaaaaaccac | cctggcgccc | 1080 |
| aatacgcaaa | ccgcctctcc | ccgcgcgttg | gccgattcat | taatgcagct | ggcacgacag | 1140 |
| gtttcccgac | tggaaagcgg | gcagtgagcg | caacgcaatt | aatgtaagtt | agcgcgaatt | 1200 |
| gatctggttt | gacagcttat | catcgactgc | acggtgcacc | aatgcttctg | gcgtcaggca | 1260 |
| gccatcggaa | gctgtggtat | ggctgtgcag | gtcgtaaatc | actgcataat | tcgtgtcgct | 1320 |
| caaggcgcac | tcccgttctg | gataatgttt | tttgcgccga | catcataacg | gttctggcaa | 1380 |
| atattctgaa | atgagctgtt | gacaattaat | catccggctc | gtataatgtg | tggaattgtg | 1440 |
| agcggataac | aatttcagaa | ttcaaaagat | cttttaagaa | ggagatatac | atatggcgag | 1500 |
| tagcgaagac | gttatcaaag | agttcatgcg | tttcaaagtt | cgtatggaag | gttccgttaa | 1560 |
| cggtcacgag | ttcgaaatcg | aaggtgaagg | tgaaggtcgt | ccgtacgaag | gtacccagac | 1620 |
| cgctaaactg | aaagttacca | aaggtggtcc | gctgccgttc | gcttgggaca | tcctgtcccc | 1680 |
| gcagttccag | tacggttcca | aagcttacgt | taaacacccg | gctgacatcc | cggactacct | 1740 |
| gaaactgtcc | ttcccggaag | gtttcaaatg | ggaacgtgtt | atgaacttcg | aagacggtgg | 1800 |
| tgttgttacc | gttacccagg | actcctccct | gcaagacggt | gagttcatct | acaaagttaa | 1860 |
| actgcgtggt | accaacttcc | cgtccgacgg | tccggttatg | cagaaaaaaa | ccatgggttg | 1920 |
| ggaagcttcc | accgaacgta | tgtacccgga | agacggtgct | ctgaaggtg | aaatcaaaat | 1980 |
| gcgtctgaaa | ctgaaagacg | gtggtcacta | cgacgctgaa | gttaaaacca | cctacatggc | 2040 |
| taaaaaaccg | gttcagctgc | cgggtgctta | caaaaccgac | atcaaactgg | acatcacctc | 2100 |
| ccacaacgaa | gactacacca | tcgttgaaca | gtacgaacgt | gctgaaggtc | gtcactccac | 2160 |
| cggtgcttaa | ggatccaaac | tcgagtaagg | atctccaggc | atcaaataaa | acgaaaggct | 2220 |

```
cagtcgaaag actgggcctt tcgttttatc tgttgtttgt cggtgaacgc tctctactag   2280
agtcacactg gctcaccttc gggtgggcct ttctgcgttt ataccctaggg cgttcggctg   2340
```

```
cagtcgaaag actgggcctt tcgttttatc tgttgtttgt cggtgaacgc tctctactag   2280
agtcacactg gctcaccttc gggtgggcct ttctgcgttt ataccctaggg cgttcggctg   2340
cggcgagcgg tatcagcagt tattggtgcc cttcgaaatg accgaccaag cgacgcccaa   2400
cctgccatca cgagatttcg attccaccgc cgccttctat gaaaggttgg gcttcggaat   2460
cgttttccgg gacgccaaca acaagaccca tcatagtttg cccccgcgac attgaccata   2520
aattcatcgc acaaaatatc gaacggggtt tatgccgctt ttagtgggtg cgaagaatag   2580
tctgctcatt acccgcgaac accgccgcat tcagatcacg cttagtagcg tccccatgag   2640
taggcagaac cgcgtccaag tccacatcat ccataacgat catgcacggg gtggaatcca   2700
cacccagact tgccagcacc tcattagcga cacgttgcgc agcggccacg tccttagcct   2760
tatccacgca atcgagaacg tactgcctaa ccgcgaaatc agactgaatc agtttccaat   2820
catcgggctt caccaaagca acagcaacgc gggttgattc gacccgttcc ggtgcttcca   2880
gaccggcgag cttgtacagt tcttcttcca tttcacgacg tacatcagcg tctatgtaat   2940
caatgcccaa agcacgctta gccccacgtg accaggacga acgcaggttt ttagaaccaa   3000
cctcatactc acgccaccga gccaccaaaa cagcgtccat atcctcgccg gcgtcgcttt   3060
gatcggccaa catatccaac atctgaaacg gcgtgtacga ccccttagac gcggttttag   3120
tagcggagcc agtcagttcc tgagacatgc ccttagcgag gtaggttgcc attttcgcag   3180
cgtctccacc ccaggtagac acctgatcaa gtttgacccc gtgctcacgc agtggcgcgt   3240
ccataccggc cttaaccaca ccagcagacc agcgggaaaa catggaatcc tcaaacgcct   3300
tgagttcatc gtcagacagt ggacgatcca agaacaacag catgttgcgg tgcaagtgcc   3360
aaccgttcgc ccaagagtct gtgacctcat agtcactata ggtgtgctcc acccgtacc    3420
gtgcacgttc tttcttccac tgagatgttt tcaccatcga agagtacgca gtcttaatac   3480
ccgcttcaac ctgcgcaaat gactgtgagc ggttgtgtcg aacagtgccc acaaacatca   3540
tgagcgcgcc acccgccgcc aagtgattct tagtagcaat agccagctca atgcggcgtt   3600
cgcccatgac ttccaattca gccagaggtg acccccagcg agagtgagag ttttgcagac   3660
cctcaaactg cgaagcaccg ttagacgacc aggacaccgc aacagcttcg tccctgcgcc   3720
acctatggca ccccgccaga gccttactat tggtgatctt gtacatgacg ttttgcctac   3780
gccacgccct agcgcgagtg acctagaaac cctcattgac ctgcggttcc ttagaggtgt   3840
tcacttctat ttcagtgtta ctcagtgtta cctagacccg atgttgtgcg gggttgcgca   3900
gtgcgagttt gtgcgggtgt tgtgcccgtt gtcttagcta gtgctatggt tgtcaattga   3960
aaccccttcg ggttatgtgg ccccgtgca tatgagttgg tagctcgcac gggggtttgt    4020
cttgtctagg gactattaat ttttagtggt gtttggtggc cgcctagctt ggctatgcgt   4080
gccagcttac ccgtactcaa tgttaaagat ttgcatcgac atgggagggt tacgtgtccg   4140
atacctaggg ggggtatccg cgactaggtg ccccggtgct cactgtctgt accggcgggg   4200
caagccccac accccgcatg gacagggtgg ctccgccccc tgcaccccca gcaatctgca   4260
tgtacatgtt ttacacatta gcacgacatg actgcatgtg catgcactgc atgcagacta   4320
ggtaaatatg agtatgtacg actagtaaca ggagcactgc acataatgaa tgagttgcag   4380
gacaatgttt gctacgcatg cgcatgacat atcgcaggaa agctactaga gtcttaaagc   4440
atggcaacca aggcacagct agaacagcaa ctacaagaag ctcaacaggc actcaggcg    4500
cagcaagcgc aggcacaagc caccatcgaa gcactagaag cgcaggcaaa ggctaagccc   4560
gtcgtggtca ccgcacgcgt tcctttggca ctacgtgagg acatgaagcg cgcaggcatg   4620
```

```
cagaacggtg aaaacctcca agagttcatg atcgccgcgt ttaccgagcg gctagaaaag    4680
ctcaccacca ccgacaacga ggaaaacaat gtctaaccca ctagttctct ttgcccaccg    4740
tgacccggta aatgacgtga cgttcgagtg cattgagcac gccacctacg acacactttc    4800
acacgctaaa gaccagatca ccgcccaaat gcaagcccta gacgaagaag ccgccctact    4860
gccctaatgg gtgtttcatg ggtgtttccc tagtgtttca tggtgttttc acctaagcta    4920
gggaattgcg cgagaagtct cgcaaaaatc agcaacccc ggaaccacac agttcacggg     4980
ggttcttcta tgccagaaat cagaaggggg aaccagtgaa cgaccccgaa tggctggatg    5040
atcctccagc gcggggatct catgctggag ttcttcgccc accccaaaag gatctaggtg    5100
aagatccttt ttgataatct catgaccaaa atcccttaac gtgagttttc gttccactga    5160
gcgtcagacc ccgtatgagc aaaaggccag caaaaggcca ggaaccgtaa aaaggccgcg    5220
ttgctggcgt ttttccatag gctccgcccc cctgacgagc atcacaaaaa tcgacgctca    5280
agtcagaggt ggcgaaaccc gacaggacta taaagatacc aggcgtttcc ccctggaagc    5340
tccctcgtgc gctctcctgt tccgaccctg ccgcttaccg gatacctgtc cgcctttctc    5400
ccttcgggaa gcgtggcgct ttctcatagc tcacgctgta ggtatctcag ttcggtgtag    5460
gtcgttcgct ccaagctggg ctgtgtgcac gaaccccccg ttcagcccga ccgctgcgcc    5520
ttatccggta actatcgtct tgagtccaac ccggtaagac acgacttatc gccactggca    5580
gcagccactg gtaacaggat tagcagagcg aggtatgtag gcggtgctac agagttcttg    5640
aagtggtggc ctaactacgg ctacactaga aggacagtat ttggtatctg cgctctgctg    5700
aagccagtta ccttcggaaa aagagttggt agctcttgat ccggcaaaca aaccaccgct    5760
ggtagcggtg gtttttttgt ttgcaagcag cagattacgc gcagaaaaaa aggatctcaa    5820
gaagatcctt tgatcttttc tacggggtct gacgctcagt ggaacgaaaa ctcacgttaa    5880
gggattttgg tcatgactag tgcttggatt ctcaccaata aaaaacgccc ggcggcaacc    5940
gagcgttctg aacaaatcca gatggagttc tgaggtcatt actggatcta tcaacaggag    6000
tccaagcgag ctcgatatca aattacgccc cgccctgcca ctcatcgcag tactgttgta    6060
attcattaag cattctgccg acatggaagc catcacaaac ggcatgatga acctgaatcg    6120
ccagcggcat cagcaccttg tcgccttgcg tataatattt gcccatggtg aaaacggggg    6180
cgaagaagtt gtccatattg gccacgttta aatcaaaact ggtgaaactc acccagggat    6240
tggctgagac gaaaaacata ttctcaataa accctttagg gaaataggcc aggttttcac    6300
cgtaacacgc cacatcttgc gaatatatgt gtagaaactg ccggaaatcg tcgtggtatt    6360
cactccagag cgatgaaaac gtttcagttt gctcatggaa aacggtgtaa caagggtgaa    6420
cactatccca tatcaccagc tcaccgtctt tcattgccat acgaaattcc ggatgagcat    6480
tcatcaggcg ggcaagaatg tgaataaagg ccggataaaa cttgtgctta ttttctttta    6540
cggtctttaa aaaggccgta atatccagct gaacggtctg gttataggta cattgagcaa    6600
ctgactgaaa tgcctcaaaa tgttctttac gatgccattg ggatatatca acggtggtat    6660
atccagtgat ttttttctcc attttagctt ccttagctcc tgaaaatctc gataactcaa    6720
aaaatacgcc cggtagtgat cttatttcat tatggtgaaa gttggaacct cttacgtgcc    6780
gatcaacgtc tcattttcgc cagatatc                                      6808
```

<210> SEQ ID NO 2
<211> LENGTH: 6057
<212> TYPE: DNA

```
<213> ORGANISM: Artificial Sequence
<220> FEATURE:
<223> OTHER INFORMATION: pBbEB2c-RFP shuttle vector
<220> FEATURE:
<221> NAME/KEY: gene
<222> LOCATION: (21)..(627)
<223> OTHER INFORMATION: terR
<220> FEATURE:
<221> NAME/KEY: promoter
<222> LOCATION: (651)..(712)
<223> OTHER INFORMATION: tetA
<220> FEATURE:
<221> NAME/KEY: promoter
<222> LOCATION: (1885)..(4280)
<223> OTHER INFORMATION: pBL1

<400> SEQUENCE: 2
gacgtcttaa gacccacttt cacatttaag ttgttttttct aatccgcata tgatcaattc      60
aaggccgaat aagaaggctg ctctgcacc ttggtgatca ataattcga tagcttgtcg        120 taataatggc ggcatactat cagtagtagg tgtttccctt tcttctttag cgacttgatg      180
ctcttgatct tccaatacgc aacctaaagt aaaatgcccc acagcgctga gtgcatataa      240
tgcattctct agtgaaaaac cttgttggca taaaaggct aattgatttt cgagagtttc       300
atactgtttt tctgtaggcc gtgtacctaa atgtactttt gctccatcgc gatgacttag     360
taaagcacat ctaaaacttt tagcgttatt acgtaaaaaa tcttgccagc tttccccttc      420
taaagggcaa aagtgagtat ggtgcctatc taacatctca atggctaagg cgtcgagcaa      480
agcccgctta ttttttacat gccaatacaa tgtaggctgc tctacaccta gcttctgggc      540
gagtttacgg gttgttaaac cttcgattcc gacctcatta agcagctcta atgcgctgtt      600
aatcacttta ctttatcta atctagacat cattaattcc taattttgt tgacactcta       660 tcgttgatag agttattta ccactcccta tcagtgatag agaaaagaat tcaaaagatc       720
ttttaagaag gagatataca tatggcgagt agcgaagacg ttatcaaaga gttcatgcgt      780
ttcaaagttc gtatggaagg ttccgttaac ggtcacgagt tcgaaatcga aggtgaaggt      840
gaaggtcgtc cgtacgaagg tacccagacc gctaaactga aagttaccaa aggtggtccg      900
ctgccgttcg cttgggacat cctgtccccg cagttccagt acggttccaa agcttacgtt      960
aaacacccgg ctgacatccc ggactacctg aaactgtcct tcccggaagg tttcaaatgg     1020
gaacgtgtta tgaacttcga agacggtggt gttgttaccg ttacccagga ctcctccctg     1080
caagacggtg agttcatcta caaagttaaa ctgcgtggta ccaacttccc gtccgacggt     1140
ccggttatgc agaaaaaaac catgggttgg gaagcttcca ccgaacgtat gtacccggaa     1200
gacggtgctc tgaaaggtga aatcaaaatg cgtctgaaac tgaaagacgg tggtcactac     1260
gacgctgaag ttaaaaccac ctacatggct aaaaaaccgg ttcagctgcc gggtgcttac     1320
aaaaccgaca tcaaactgga catcacctcc cacaacgaag actacaccat cgttgaacag     1380
tacgaacgtg ctgaaggtcg tcactccacc ggtgcttaag gatccaaact cgagtaagga     1440
tctccaggca tcaaataaaa cgaaaggctc agtcgaaaga ctgggccttt cgttttatct     1500
gttgtttgtc ggtgaacgct ctctactaga gtcacactgg ctcaccttcg ggtgggcctt     1560
tctgcgttta tacctagggc gttcggctgc ggcgagcggt atcagcagtt attggtgccc     1620
ttcgaaatga ccgaccaagc gacgcccaac ctgccatcac gagatttcga ttccaccgcc     1680
gccttctatg aaaggttggg cttcggaatc gttttccggg acgccaacaa caagacccat     1740
catagtttgc ccccgcgaca ttgaccataa attcatcgca caaatatcg aacgggtttt      1800 atgccgcttt tagtgggtgc gaagaatagt ctgctcatta cccgcgaaca ccgccgcatt     1860
```

```
cagatcacgc ttagtagcgt ccccatgagt aggcagaacc gcgtccaagt ccacatcatc    1920
cataacgatc atgcacgggg tggaatccac acccagactt gccagcacct cattagcgac    1980
acgttgcgca gcggccacgt ccttagcctt atccacgcaa tcgagaacgt actgcctaac    2040
cgcgaaatca gactgaatca gtttccaatc atcgggcttc accaaagcaa cagcaacgcg    2100
ggttgattcg acccgttccg gtgcttccag accggcgagc ttgtacagtt cttcttccat    2160
ttcacgacgt acatcagcgt ctatgtaatc aatgcccaaa gcacgcttag ccccacgtga    2220
ccaggacgaa cgcaggtttt tagaaccaac ctcatactca cgccaccgag ccaccaaaac    2280
agcgtccata tcctcgccgg cgtcgctttg atcggccaac atatccaaca tctgaaacgg    2340
cgtgtacgac cccttagacg cggttttagt agcggagcca gtcagttcct gagacatgcc    2400
cttagcgagg taggttgcca ttttcgcagc gtctccaccc caggtagaca cctgatcaag    2460
tttgaccccg tgctcacgca gtggcgcgtc cataccggcc ttaaccacac cagcagacca    2520
gcgggaaaac atggaatcct caaacgcctt gagttcatcg tcagacagtg gacgatccaa    2580
gaacaacagc atgttgcggt gcaagtgcca accgttcgcc caagagtctg tgacctcata    2640
gtcactatag gtgtgctcca ccccgtaccg tgcacgttct ttcttccact gagatgtttt    2700
caccatcgaa gagtacgcag tcttaatacc cgcttcaacc tgcgcaaatg actgtgagcg    2760
gttgtgtcga acagtgccca caaacatcat gagcgcgcca cccgccgcca agtgattctt    2820
agtagcaata gccagctcaa tgcggcgttc gcccatgact tccaattcag ccagaggtga    2880
cccccagcga gagtgagagt tttgcagacc ctcaaactgc gaagcaccgt tagacgacca    2940
ggacaccgca acagcttcgt ccctgcgcca cctatggcac cccgccagag ccttactatt    3000
ggtgatcttg tacatgacgt tttgcctacg ccacgcccta gcgcgagtga ccttagaacc    3060
ctcattgacc tgcggttcct tagaggtgtt cacttctatt tcagtgttac tcagtgttac    3120
ctagacccga tgttgtgcgg ggttgcgcag tgcgagtttg tgcgggtgtt gtgcccgttg    3180
tcttagctag tgctatggtt gtcaattgaa acccctttcgg gttatgtggc ccccgtgcat    3240
atgagttggt agctcgcacg ggggtttgtc ttgtctaggg actattaatt tttagtggtg    3300
tttggtggcc gcctagcttg gctatgcgtg ccagcttacc cgtactcaat gttaaagatt    3360
tgcatcgaca tgggagggtt acgtgtccga tacctagggg gggtatccgc gactaggtgc    3420
cccggtgctc actgtctgta ccggcggggc aagcccaca ccccgcatgg acagggtggc    3480
tccgccccct gcaccccag caatctgcat gtacatgttt tacacattag cacgacatga    3540
ctgcatgtgc atgcactgca tgcagactag gtaaatatga gtatgtacga ctagtaacag    3600
gagcactgca cataatgaat gagttgcagg acaatgtttg ctacgcatgc gcatgacata    3660
tcgcaggaaa gctactagag tcttaaagca tggcaaccaa ggcacagcta gaacagcaac    3720
tacaagaagc tcaacaggca ctacaggcgc agcaagcgca ggcacaagcc accatcgaag    3780
cactagaagc gcaggcaaag gctaagcccg tcgtggtcac cgcacgcgtt cctttggcac    3840
tacgtgagga catgaagcgc gcaggcatgc agaacggtga aaacctccaa gagttcatga    3900
tcgccgcgtt taccgagcgg ctagaaaagc tcaccaccac cgacaacgag gaaaacaatg    3960
tctaacccac tagttctctt tgcccaccgt gacccggtaa atgacgtgac gttcgagtgc    4020
attgagcacg ccacctacga cacactttca cacgctaaag accagatcac cgcccaaatg    4080
caagccctag acgaagaagc cgccctactg ccctaatggg tgtttcatgg gtgtttccct    4140
agtgtttcat ggtgttttca cctaagctag ggaattgcgc gagaagtctc gcaaaaatca    4200
```

```
gcaaccccg gaaccacaca gttcacgggg gttcttctat gccagaaatc agaaagggga      4260
accagtgaac gaccccgaat ggctggatga tcctccagcg cggggatctc atgctggagt      4320
tcttcgccca ccccaaaagg atctaggtga agatcctttt tgataatctc atgaccaaaa      4380
tcccttaacg tgagttttcg ttccactgag cgtcagaccc cgtatgagca aaaggccagc      4440
aaaaggccag gaaccgtaaa aaggccgcgt tgctggcgtt tttccatagg ctccgccccc      4500
ctgacgagca tcacaaaaat cgacgctcaa gtcagaggtg cgaaacccg acaggactat      4560
aaagatacca ggcgtttccc cctggaagct ccctcgtgcg ctctcctgtt ccgaccctgc      4620
cgcttaccgg atacctgtcc gcctttctcc cttcgggaag cgtggcgctt tctcatagct      4680
cacgctgtag gtatctcagt tcggtgtagg tcgttcgctc caagctgggc tgtgtgcacg      4740
aaccccccgt tcagcccgac cgctgcgcct tatccggtaa ctatcgtctt gagtccaacc      4800
cggtaagaca cgacttatcg ccactggcag cagccactgg taacaggatt agcagagcga      4860
ggtatgtagg cggtgctaca gagttcttga agtggtggcc taactacggc tacactagaa      4920
ggacagtatt tggtatctgc gctctgctga agccagttac cttcggaaaa agagttggta      4980
gctcttgatc cggcaaacaa accaccgctg gtagcggtgg tttttttgtt tgcaagcagc      5040
agattacgcg cagaaaaaaa ggatctcaag aagatccttt gatcttttct acggggtctg      5100
acgctcagtg gaacgaaaac tcacgttaag ggattttggt catgactagt gcttggattc      5160
tcaccaataa aaaacgcccg gcggcaaccg agcgttctga caaatccag atggagttct      5220
gaggtcatta ctggatctat caacaggagt ccaagcgagc tcgatatcaa attacgcccc      5280
gccctgccac tcatcgcagt actgttgtaa ttcattaagc attctgccga catggaagcc      5340
atcacaaacg gcatgatgaa cctgaatcgc cagcggcatc agcaccttgt cgccttgcgt      5400
ataatatttg cccatggtga aaacggggc gaagaagttg tccatattgg ccacgtttaa      5460
atcaaaactg gtgaaactca cccagggatt ggctgagacg aaaaacatat tctcaataaa      5520
ccctttaggg aaataggcca ggttttcacc gtaacacgcc acatcttgcg aatatatgtg      5580
tagaaactgc cggaaatcgt cgtggtattc actccagagc gatgaaaacg tttcagtttg      5640
ctcatggaaa acggtgtaac aagggtgaac actatcccat atcaccagct caccgtcttt      5700
cattgccata cgaaattccg gatgagcatt catcaggcgg gcaagaatgt gaataaaggc      5760
cggataaaac ttgtgcttat ttttctttac ggtctttaaa aaggccgtaa tatccagctg      5820
aacggtctgg ttataggtac attgagcaac tgactgaaat gcctcaaaat gttctttacg      5880
atgccattgg gatatatcaa cggtggtata tccagtgatt ttttctcca ttttagcttc      5940
cttagctcct gaaaatctcg ataactcaaa aaatacgccc ggtagtgatc ttatttcatt      6000
atggtgaaag ttggaacctc ttacgtgccg atcaacgtct cattttcgcc agatatc       6057
```

```
<210> SEQ ID NO 3
<211> LENGTH: 6930
<212> TYPE: DNA
<213> ORGANISM: Artificial Sequence
<220> FEATURE:
<223> OTHER INFORMATION: pBbEB5c-RFP shuttle vector
<220> FEATURE:
<221> NAME/KEY: gene
<222> LOCATION: (49)..(1140)
<223> OTHER INFORMATION: lacI
<220> FEATURE:
<221> NAME/KEY: promoter
<222> LOCATION: (1232)..(1585)
<223> OTHER INFORMATION: LacUV5 promoter
<220> FEATURE:
<221> NAME/KEY: promoter
```

<222> LOCATION: (2599)..(5153)
<223> OTHER INFORMATION: pBL1 promoter

<400> SEQUENCE: 3

```
gacgtcggtg cctaatgagt gagctaactt acattaattg cgttgcgctc actgcccgct      60
ttccagtcgg gaaacctgtc gtgccagctg cattaatgaa tcggccaacg cgcggggaga     120
ggcggtttgc gtattgggcg ccagggtggt ttttcttttc accagtgaga cgggcaacag     180
ctgattgccc ttcaccgcct ggccctgaga gagttgcagc aagcggtcca cgctggtttg     240
ccccagcagg cgaaaatcct gtttgatggt ggttaacggc gggatataac atgagctgtc     300
ttcggtatcg tcgtatccca ctaccgagat gtccgcacca acgcgcagcc cggactcggt     360
aatggcgcgc attgcgccca cgccatctg atcgttggca accagcatcg cagtgggaac      420
gatgccctca ttcagcattt gcatggtttg ttgaaaaccg gacatggcac tccagtcgcc     480
ttcccgttcc gctatcggct gaatttgatt gcgagtgaga tatttatgcc agccagccag     540
acgcagacgc gccgagacag aacttaatgg gcccgctaac agcgcgattt gctggtgacc     600
caatgcgacc agatgctcca cgcccagtcg cgtaccgtct tcatgggaga aaataatact     660
gttgatgggt gtctggtcag agacatcaag aaataacgcc ggaacattag tgcaggcagc     720
ttccacagca atggcatcct ggtcatccag cggatagtta atgatcagcc cactgacgcg     780
ttgcgcgaga gattgtgca ccgccgcttt acaggcttcg acgccgcttc gttctaccat      840
cgacaccacc acgctggcac ccagttgatc ggcgcgagat ttaatcgccg cgacaatttg     900
cgacggcgcg tgcagggcca gactggaggt ggcaacgcca atcagcaacg actgtttgcc     960
cgccagttgt tgtgccacgc ggttgggaat gtaattcagc tccgccatcg ccgcttccac    1020
ttttcccgc gttttcgcag aaacgtggct ggcctggttc accacgcggg aaacggtctg     1080
ataagagaca ccggcatact ctgcgacatc gtataacgtt actggtttca cattcaccac    1140
cctgaattga ctctcttccg ggcgctatca tgccataccg cgaaaggttt tgcgccattc    1200
gatggtgtcc gggatctcga cgctctccct tatgcgactc ctgcattagg aagcagccca    1260
gtagtaggtt gaggccgttg agcaccgccg ccgcaaggaa tggtgcatgc aaggagatgg    1320
cgcccaacag tcccccggcc acggggcctg ccaccatacc cacgccgaaa caagcgctca    1380
tgagcccgaa gtggcgagcc cgatcttccc catcggtgat gtcggcgata taggcgccag    1440
caaccgcacc tgtggcgccg gtgatgccgg ccacgatgcg tccggcgtag aggatcgaga    1500
tcgtttaggc accccaggct ttacacttta tgcttccggc tcgtataatg tgtggaattg    1560
tgagcggata acaatttcag aattcaaaag atcttttaag aaggagatat acatatggcg    1620
agtagcgaag acgttatcaa agagttcatg cgtttcaaag ttcgtatgga aggttccgtt    1680
aacggtcacg agttcgaaat cgaaggtgaa ggtgaaggtc gtccgtacga aggtacccag    1740
accgctaaac tgaaagttac caaaggtggt ccgctgccgt tcgcttggga catcctgtcc    1800
ccgcagttcc agtacggttc caaagcttac gttaaacacc cggctgacat cccggactac    1860
ctgaaactgt ccttcccgga aggtttcaaa tgggaacgtg ttatgaactt cgaagacggt    1920
ggtgttgtta ccgttacccca ggactcctcc ctgcaagacg gtgagttcat ctacaaagtt    1980
aaactgcgtg gtaccaactt cccgtccgac ggtccggtta tgcagaaaaa aaccatgggt    2040
tgggaagctt ccaccgaacg tatgtacccg gaagacggtg ctctgaaagg tgaaatcaaa    2100
atgcgtctga aactgaaaga cggtggtcac tacgacgctg aagttaaaac cacctacatg    2160
gctaaaaaac cggttcagct gccgggtgct tacaaaaccg catcaaaact ggacatcacc    2220
```

-continued

```
tcccacaacg aagactacac catcgttgaa cagtacgaac gtgctgaagg tcgtcactcc    2280
accggtgctt aaggatccaa actcgagtaa ggatctccag gcatcaaata aaacgaaagg    2340
ctcagtcgaa agactgggcc tttcgtttta tctgttgttt gtcggtgaac gctctctact    2400
agagtcacac tggctcacct tcgggtgggc ctttctgcgt ttatacctag ggcgttcggc    2460
tgcggcgagc ggtatcagca gttattggtg cccttcgaaa tgaccgacca agcgacgccc    2520
aacctgccat cacgagattt cgattccacc gccgccttct atgaaaggtt gggcttcgga    2580
atcgttttcc gggacgccaa caacaagacc catcatagtt tgccccgcg acattgacca     2640
taaattcatc gcacaaaata tcgaacgggg tttatgccgc ttttagtggg tgcgaagaat    2700
agtctgctca ttacccgcga acaccgccgc attcagatca cgcttagtag cgtccccatg    2760
agtaggcaga accgcgtcca agtccacatc atccataacg atcatgcacg gggtggaatc    2820
cacacccaga cttgccagca cctcattagc gacacgttgc gcagcggcca cgtccttagc    2880
cttatccacg caatcgagaa cgtactgcct aaccgcgaaa tcagactgaa tcagtttcca    2940
atcatcgggc ttcaccaaag caacagcaac gcgggttgat tcgacccgtt ccggtgcttc    3000
cagaccggcg agcttgtaca gttcttcttc catttcacga cgtacatcag cgtctatgta    3060
atcaatgccc aaagcacgct tagccccacg tgaccaggac gaacgcaggt ttttagaacc    3120
aacctcatac tcacgccacc gagccaccaa aacagcgtcc atatcctcgc cggcgtcgct    3180
ttgatcggcc aacatatcca acatctgaaa cggcgtgtac gacccttag acgcggtttt     3240
agtagcggag ccagtcagtt cctgagacat gcccttagcg aggtaggttg ccattttcgc    3300
agcgtctcca ccccaggtag acacctgatc aagtttgacc ccgtgctcac gcagtggcgc    3360
gtccataccg gccttaacca caccagcaga ccagcgggaa acatggaat cctcaaacgc      3420
cttgagttca tcgtcagaca gtggacgatc caagaacaac agcatgttgc ggtgcaagtg    3480
ccaaccgttc gcccaagagt ctgtgacctc atagtcacta taggtgtgct ccaccccgta    3540
ccgtgcacgt tctttcttcc actgagatgt tttcaccatc gaagagtacg cagtcttaat    3600
acccgcttca acctgcgcaa atgactgtga gcggttgtgt cgaacagtgc ccacaaacat    3660
catgagcgcg ccaccgccg ccaagtgatt cttagtagca atagccagct caatgcggcg      3720
ttcgcccatg acttccaatt cagccagagg tgaccccag cgagagtgag agttttgcag      3780
accctcaaac tgcgaagcac cgttagcga ccaggacacc gcaacagctt cgtccctgcg      3840
ccacctatgg cacccgcca gagccttact attggtgatc ttgtacatga cgttttgcct      3900
acgccacgcc ctagcgcgag tgaccttaga accctcattg acctgcggtt ccttagaggt    3960
gttcacttct atttcagtgt tactcagtgt taccagacc cgatgttgtg cggggttgcg      4020
cagtgcgagt ttgtgcgggt gttgtgcccg ttgtcttagc tagtgctatg gttgtcaatt    4080
gaaacccctt cgggttatgt ggccccgtg catatgagtt ggtagctcgc acgggggttt      4140
gtcttgtcta gggactatta attttagtg gtgtttggtg gccgcctagc ttggctatgc      4200
gtgccagctt acccgtactc aatgttaaag atttgcatcg acatgggagg gttacgtgtc    4260
cgatacctag gggggtatc cgcgactagg tgccccggtg ctcactgtct gtaccggcgg      4320
ggcaagcccc acacccgca tggacagggt ggctccgccc cctgcacccc cagcaatctg      4380
catgtacatg ttttacacat tagcacgaca tgactgcatg tgcatgcact gcatgcagac    4440
taggtaaata tgagtatgta cgactagtaa caggagcact gcacataatg aatgagttgc    4500
aggacaatgt ttgctacgca tgcgcatgac atatcgcagg aaagctacta gagtcttaaa    4560
gcatggcaac caaggcacag ctagaacagc aactacaaga agctcaacag gcactacagg    4620
```

```
cgcagcaagc gcaggcacaa gccaccatcg aagcactaga agcgcaggca aaggctaagc    4680
ccgtcgtggt caccgcacgc gttcctttgg cactacgtga ggacatgaag cgcgcaggca    4740
tgcagaacgg tgaaaacctc caagagttca tgatcgccgc gtttaccgag cggctagaaa    4800
agctcaccac caccgacaac gaggaaaaca atgtctaacc cactagttct ctttgcccac    4860
cgtgacccgg taaatgacgt gacgttcgag tgcattgagc acgccaccta cgacacactt    4920
tcacacgcta aagaccagat caccgcccaa atgcaagccc tagacgaaga agccgcccta    4980
ctgccctaat gggtgtttca tgggtgtttc cctagtgttt catggtgttt tcacctaagc    5040
tagggaattg cgcgagaagt ctcgcaaaaa tcagcaaccc ccggaaccac acagttcacg    5100
ggggttcttc tatgccagaa atcagaaagg ggaaccagtg aacgaccccg aatggctgga    5160
tgatcctcca gcgcggggat ctcatgctgg agttcttcgc ccaccccaaa aggatctagg    5220
tgaagatcct ttttgataat ctcatgacca aaatcccttaa cgtgagtttt cgttccact    5280 gagcgtcaga ccccgtatga gcaaaaggcc agcaaaaggc caggaaccgt aaaaaggccg    5340
cgttgctggc gttttttccat aggctccgcc ccctgacga gcatcacaaa aatcgacgct    5400
caagtcagag gtggcgaaac ccgacaggac tataaagata caggcgtttt ccccctggaa    5460
gctccctcgt gcgctctcct gttccgaccc tgccgcttac cggatacctg tccgcctttc    5520
tcccttcggg aagcgtggcg ctttctcata gctcacgctg taggtatctc agttcggtgt    5580
aggtcgttcg ctccaagctg ggctgtgtgc acgaaccccc cgttcagccc gaccgctgcg    5640
ccttatccgg taactatcgt cttgagtcca acccggtaag acacgactta tcgccactgg    5700
cagcagccac tggtaacagg attagcagag cgaggtatgt aggcggtgct acagagttct    5760
tgaagtggtg gcctaactac ggctacacta aaggacagt attggtatc tgcgctctgc    5820 tgaagccagt taccttcgga aaaagagttg gtagctcttg atccggcaaa caaaccaccg    5880
ctggtagcgg tggttttttt gtttgcaagc agcagattac gcgcagaaaa aaaggatctc    5940
aagaagatcc tttgatcttt tctacggggt ctgacgctca gtggaacgaa aactcacgtt    6000
aagggatttt ggtcatgact agtgcttgga ttctcaccaa taaaaaacgc ccggcggcaa    6060
ccgagcgttc tgaacaaatc cagatggagt tctgaggtca ttactggatc tatcaacagg    6120
agtccaagcg agctcgatat caaattacgc cccgccctgc cactcatcgc agtactgttg    6180
taattcatta agcattctgc cgacatgaa gccatcacaa acggcatgat gaacctgaat    6240
cgccagcggc atcagcacct tgtcgccttg cgtataatat ttgcccatgg tgaaaacggg    6300
ggcgaagaag ttgtccatat tggccacgtt taaatcaaaa ctggtgaaac tcacccaggg    6360
attggctgag acgaaaaaca tattctcaat aaacccttta gggaaatagg ccaggttttc    6420
accgtaacac gccacatctt gcgaatatat gtgtagaaac tgccggaaat cgtcgtggta    6480
ttcactccag agcgatgaaa acgtttcagt ttgctcatgg aaaacggtgt aacaagggtg    6540
aacactatcc catatcacca gctcaccgtc tttcattgcc atacgaaatt ccggatgagc    6600
attcatcagg cgggcaagaa tgtgaataaa ggccggataa aacttgtgct tattttttctt    6660 tacggtcttt aaaaaggccg taatatccag ctgaacggtc tggttatagg tacattgagc    6720
aactgactga aatgcctcaa aatgttcttt acgatgccat tgggatatat caacggtggt    6780
atatccagtg atttttttct ccatttttagc ttccttagct cctgaaaatc tcgataactc    6840
aaaaaatacg cccggtagtg atcttatttc attatggtga agttggaac ctcttacgtg    6900 ccgatcaacg tctcatttttc gccagatatc                                    6930
```

<210> SEQ ID NO 4
<211> LENGTH: 4051
<212> TYPE: DNA
<213> ORGANISM: Artificial Sequence
<220> FEATURE:
<223> OTHER INFORMATION: pBbE1c-RFP

<400> SEQUENCE: 4

```
gacgtcgaca ccatcgaatg gtgcaaaacc tttcgcggta tggcatgata gcgcccggaa      60
gagagtcaat tcagggtggt gaatgtgaaa ccagtaacgt tatacgatgt cgcagagtat     120
gccggtgtct cttatcagac cgtttcccgc gtggtgaacc aggccagcca cgtttctgcg     180
aaaacgcggg aaaaagtgga agcggcgatg gcggagctga attacattcc caaccgcgtg     240
gcacaacaac tggcgggcaa acagtcgttg ctgattggcg ttgccacctc cagtctggcc     300
ctgcacgcgc cgtcgcaaat tgtcgcggcg attaaatctc gcgccgatca actgggtgcc     360
agcgtggtgg tgtcgatggt agaacgaagc ggcgtcgaag cctgtaaagc ggcggtgcac     420
aatcttctcg cgcaacgcgt cagtgggctg atcattaact atccgctgga tgaccaggat     480
gccattgctg tggaagctgc ctgcactaat gttccggcgt tatttcttga tgtctctgac     540
cagacaccca tcaacagtat tatttttctc catgaagacg gtacgcgact gggcgtggag     600
catctggtcg cattgggtca ccagcaaatc gcgctgttag cgggcccatt aagttctgtc     660
tcggcgcgtc tgcgtctggc tggctggcat aaatatctca ctcgcaatca aattcagccg     720
atagcggaac gggaaggcga ctggagtgcc atgtccggtt ttcaacaaac catgcaaatg     780
ctgaatgagg gcatcgttcc cactgcgatg ctggttgcca acgatcagat ggcgctgggc     840
gcaatgcgcg ccattaccga gtccgggctg cgcgttggtg cggatatctc ggtagtggga     900
tacgacgata ccgaagacag ctcatgttat atcccgccgt taaccaccat caaacaggat     960
tttcgcctgc tggggcaaac cagcgtggac cgcttgctgc aactctctca gggccaggcg    1020
gtgaagggca atcagctgtt gcccgtctca ctggtgaaaa gaaaaaccac cctggcgccc    1080
aatacgcaaa ccgcctctcc ccgcgcgttg gccgattcat taatgcagct ggcacgacag    1140
gtttcccgac tggaaagcgg gcagtgagcg caacgcaatt aatgtaagtt agcgcgaatt    1200
gatctggttt gacagcttat catcgactgc acggtgcacc aatgcttctg gcgtcaggca    1260
gccatcggaa gctgtggtat ggctgtgcag tcgtaaatc actgcataat tcgtgtcgct    1320
caaggcgcac tcccgttctg gataatgttt tttgcgccga catcataacg gttctggcaa    1380
atattctgaa atgagctgtt gacaattaat catccggctc gtataatgtg tggaattgtg    1440
agcggataac aatttcagaa ttcaaaagat cttttaagaa ggagatatac atatggcgag    1500
tagcgaagac gttatcaaag agttcatgcg tttcaaagtt cgtatggaag gttccgttaa    1560
cggtcacgag ttcgaaatcg aaggtgaagg tgaaggtcgt ccgtacgaag gtacccagac    1620
cgctaaactg aaagttacca aaggtggtcc gctgccgttc gcttgggaca tcctgtcccc    1680
gcagttccag tacggttcca agcttacgt taaacacccg gctgacatcc cggactacct    1740
gaaactgtcc ttcccggaag gtttcaaatg ggaacgtgtt atgaacttcg aagacggtgg    1800
tgttgttacc gttacccagg actcctccct gcaagacggt gagttcatct acaaagttaa    1860
actgcgtggt accaacttcc cgtccgacgg tccggttatg cagaaaaaaa ccatgggttg    1920
```

```
ggaagcttcc accgaacgta tgtacccgga agacggtgct ctgaaaggtg aaatcaaaat    1980
gcgtctgaaa ctgaaagacg gtggtcacta cgacgctgaa gttaaaacca cctacatggc    2040
taaaaaaccg gttcagctgc cgggtgctta caaaaccgac atcaaactgg acatcacctc    2100
ccacaacgaa gactacacca tcgttgaaca gtacgaacgt gctgaaggtc gtcactccac    2160
cggtgcttaa ggatccaaac tcgagtaagg atctccaggc atcaaataaa acgaaaggct    2220
cagtcgaaag actgggcctt tcgttttatc tgttgtttgt cggtgaacgc tctctactag    2280
agtcacactg gctcaccttc gggtgggcct ttctgcgttt atacctaggg cgttcggctg    2340
cggcgagcgg tatcagctca ctcaaaggcg gtaatacggt tatccacaga atcaggggat    2400
aacgcaggaa agaacatgtg agcaaaaggc cagcaaaagg ccaggaaccg taaaaaggcc    2460
gcgttgctgg cgtttttcca taggctccgc cccccctgacg agcatcacaa aaatcgacgc    2520
tcaagtcaga ggtggcgaaa cccgacagga ctataaagat accaggcgtt ccccctgga    2580 agctccctcg tgcgctctcc tgttccgacc ctgccgctta ccggatacct gtccgccttt    2640
ctcccttcgg gaagcgtggc gctttctcat agctcacgct gtaggtatct cagttcggtg    2700
taggtcgttc gctccaagct gggctgtgtg cacgaacccc ccgttcagcc cgaccgctgc    2760
gccttatccg gtaactatcg tcttgagtcc aacccggtaa gacacgactt atcgccactg    2820
gcagcagcca ctggtaacag gattagcaga gcgaggtatg taggcggtgc tacagagttc    2880
ttgaagtggt ggcctaacta cggctacact agaaggacag tatttggtat ctgcgctctg    2940
ctgaagccag ttaccttcgg aaaaagagtt ggtagctctt gatccggcaa acaaaccacc    3000
gctggtagcg gtggtttttt tgtttgcaag cagcagatta cgcgcagaaa aaaggatct    3060 caagaagatc ctttgatctt ttctacgggg tctgacgctc agtggaacga aaactcacgt    3120
taagggattt tggtcatgac tagtgcttgg attctcacca ataaaaaacg cccgcggca    3180 accgagcgtt ctgaacaaat ccagatggag ttctgaggtc attactggat ctatcaacag    3240
gagtccaagc gagctcgata tcaaattacg ccccgccctg ccactcatcg cagtactgtt    3300
gtaattcatt aagcattctg ccgacatgga agccatcaca aacggcatga tgaacctgaa    3360
tcgccagcgg catcagcacc ttgtcgcctt gcgtataata tttgcccatg gtgaaaacgg    3420
gggcgaagaa gttgtccata ttggccacgt ttaaatcaaa actggtgaaa ctcacccagg    3480
gattggctga cgaaaaac atattctcaa taaacccttt agggaaatag gccaggtttt    3540
caccgtaaca cgccacatct tgcgaatata tgtgtagaaa ctgccggaaa tcgtcgtggt    3600
attcactcca gagcgatgaa aacgtttcag tttgctcatg gaaaacggtg taacaagggt    3660
gaacactatc ccatatcacc agctcaccgt cttttcattgc catacgaaat tccggatgag    3720
cattcatcag gcgggcaaga atgtgaataa aggccggata aaacttgtgc ttatttttct    3780
ttacggtctt taaaaaggcc gtaatatcca gctgaacggt ctggtatag gtacattgag    3840 caactgactg aaatgcctca aaatgttctt tacgatgcca ttgggatata tcaacggtgg    3900
tatatccagt gattttttc tccatttag cttccttagc tcctgaaaat ctcgataact    3960
caaaaaatac gcccggtagt gatcttattt cattatggtg aaagttggaa cctcttacgt    4020
gccgatcaac gtctcatttt cgccagatat c                                   4051
```

SHUTTLE VECTOR FOR *CORYNEBACTERIUM* OR *E. COLI*

CROSS-REFERENCE TO RELATED APPLICATION

This application claims priority to Korean Patent Application No. 10-2014-0146255, filed on Oct. 27, 2014, and all the benefits accruing therefrom under 35 U.S.C. §119, the contents of which in its entirety are herein incorporated by reference.

BACKGROUND

1. Field

The present disclosure relates to a shuttle vector that can be used for both *Corynebacterium* and *E. coli*, a host cell transformed with the shuttle vector, a method for producing a substance using the transformed host cell and a multi-shuttle vector using the shuttle vector.

[Description about National Research and Development Support]

This study was supported by Ministry of Science, ICT and Future Planning, Republic of Korea (Cooperation research project: Creative Amalgamation Research, Project No. CAP-11-1-KIST) under the superintendence of the Fundamental technology research society.

2. Description of the Related Art

At present, the newest metabolic engineering techniques such as next-generation genome sequencing and fast DNA synthesis are used to produce useful bioproducts. Bioproduct production using *E. coli* and yeast, which are the most widely employed industrially at present, has been being developed consistently. For production of foreign metabolites, reconstruction of heterologous genes into cells is an essential process. Also, an optimizing process is necessary to maximize the production of target substances. A usual method of introducing a heterologous metabolic pathway for production of a target substance is to insert a specific gene into a plasmid or a genome. More recently, sequence- and ligase-independent cloning (SLIC), Gibson DNA assembly, circular polymerase extension cloning (CPEC), etc. are used as advanced cloning methods.

SUMMARY

In an aspect, the present disclosure is directed to providing a shuttle vector that can operate in both *Corynebacterium* and *E. coli*.

In another aspect, the present disclosure is directed to providing a vector that can express two or more proteins at the same time, with two or more target genes inserted therein.

In another aspect, the present disclosure is directed to providing a vector that can operate effectively in industrially useful *Corynebacterium glutamicum*.

In another aspect, the present disclosure is directed to providing an expression vector that can effectively produce industrially useful substances and a host cell transformed with the vector.

In another aspect, the present disclosure is directed to providing a method for effectively producing industrially useful substances.

In another aspect, the present disclosure is directed to providing a method for preparing a multi-shuttle vector that can express two or more target proteins which can invoke a mechanism for producing useful substances or which themselves are industrially useful.

In another aspect, the present disclosure is directed to providing a vector that can sustain strong expression even when the host cell is in a stationary phase.

In an aspect, the present disclosure provides a shuttle vector for *Corynebacterium* and *E. coli*, containing: a repressor selected from a group consisting of a lacI repressor and a tetR repressor; a promoter selected from a group consisting of a trc promoter, a tetA promoter and a LacUV5 promoter; a replication origin pBL1 derived from *Corynebacterium glutamicum*; and a replication origin ColE1 of *E. coli*.

In an aspect, the present disclosure provides a host cell transformed with the shuttle vector.

In an aspect, the present disclosure provides a method for producing a substance, including culturing the transformed host cell.

In an aspect, the present disclosure provides a method for preparing a multi-shuttle vector containing two or more target genes, including inserting a target gene into the shuttle vector according to an exemplary embodiment of the present disclosure, wherein the shuttle vector already contains one or more target gene (i.e., "pre-existing target gene") before the insertion of the target gene, and the step of inserting includes forming complementary binding between the BglII site located upstream of the pre-existing target gene of the shuttle vector or the target gene to be inserted into the shuttle vector and the BamHI site located downstream of the pre-existing target gene or another target gene to be inserted into the shuttle vector.

The vector disclosed in the present disclosure may be used to produce various chemicals and amino acids. Specifically, it can express two or more target proteins which can invoke a mechanism for producing useful substances or which themselves may be industrially useful. In another aspect, the vector provided by the present disclosure can sustain strong expression even when the host cell is in a stationary phase. In addition, time and cost can be saved greatly and the level of gene expression can be effectively controlled owing to simple gene assembly.

BRIEF DESCRIPTION OF THE DRAWINGS

FIG. 9a and FIG. 9b show the sequence of a pBbEB1c-RFP vector according to an exemplary embodiment of the present disclosure. The underlined portions indicate lacI (76-1167), pTrc (1224-1463) and pBL1 (2477-5031), in that order.

FIG. 10a and FIG. 10b show the sequence of a pBbEB2c-RFP vector according to an exemplary embodiment of the present disclosure. The underlined portions indicate tetR (21-627), tetA (651-712) and pBL1 (1885-4280), in that order.

FIG. 11a and FIG. 11b show the sequence of a pBbEB5c-RFP vector according to an exemplary embodiment of the present disclosure. The underlined portions indicate lacI (49-1140), LacUV5 (1232-1585) and pBL1 (2599-5153), in that order.

DETAILED DESCRIPTION

Figure 1:
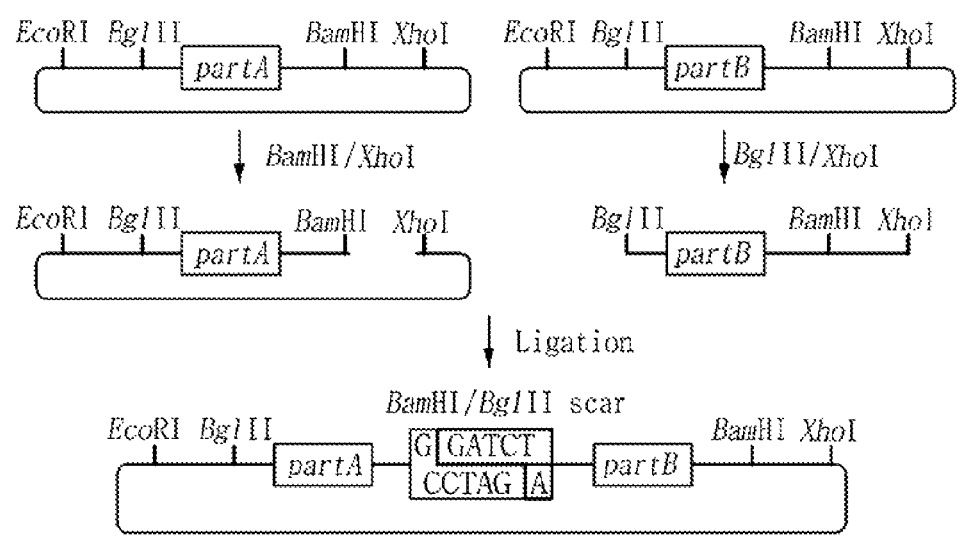
FIG. 1 schematically illustrates BglBrick cloning.

In the present disclosure, a "multi-shuttle vector" refers to a shuttle vector which contains two or more target genes or two or more kinds of target genes desired to be overexpressed and can express two or more target proteins or two or more kinds of target proteins at the same time upon transformation. The expressed two or more proteins may be used as they are or the two or more proteins may invoke a mechanism for producing desired useful substances.

Genes within all the vectors disclosed in the present disclosure are operably linked with each other. The term "operable" means that the target gene can be expressed normally.

In an aspect, the present disclosure provides a shuttle vector for *Corynebacterium* and *E. coli*, containing: a repressor selected from a group consisting of a lacI repressor and a tetR repressor; a promoter selected from a group consisting of a trc promoter, a tetA promoter and a LacUV5 promoter; a replication origin pBL1 derived from *Corynebacterium glutamicum*; and a replication origin ColE1 of *E. coli*.

Since the vector can be used both for *Corynebacterium* and *E. coli*, it is possible to easily recombine a gene in *E. coli* and to obtain a desired protein in a *Corynebacterium* strain through transformation.

For example, a template vector of the shuttle vector for *Corynebacterium* and *E. coli* may be pBbE1c-RFP (Lee T S, Krupa R A, Zhang F, Hajimorad M, Holtz W J, Prasad N, Lee S K, Keasling J D (2011b) BglBrick vectors and datasheets: a synthetic biology platform for gene expression. *J Biol Eng* 5:12). Also, the repressor and the promoter may be ones derived, for example, from pBbA2k-RFP and/or pBbE5c-RFP (Lee T S, Krupa R A, Zhang F, Hajimorad M, Holtz W J, Prasad N, Lee S K, Keasling J D (2011b) BglBrick vectors and datasheets: a synthetic biology platform for gene expression. *J Biol Eng* 5:12). Also, the replication origin pBL1 derived from *Corynebacterium glutamicum* may be one derived, for example, from pXMJ19 (Jakoby M et al., (1999) "Construction and application of new *Corynebacterium glutamicum* vectors." *Biotechnology Techniques* 13, 437-441).

In an aspect, the vector may further contain a chloramphenicol-resistant reporter gene.

In another aspect, the vector may further contain a red fluorescent protein (RFP) gene. Since the red fluorescent protein (RFP) gene emits fluorescence when expressed in a host cell, it informs that the vector operates normally and the target gene has been expressed normally. Another target gene may be inserted at the site of the red fluorescent protein (RFP) gene. The vector may contain a BglII site and a BamHI site as restriction enzyme sites on both sides of the red fluorescent protein (RFP) gene.

For example, the chloramphenicol-resistant reporter gene and the red fluorescent protein (RFP) gene may be ones derived from the template vector pBbE1c-RFP (Lee T S, Krupa R A, Zhang F, Hajimorad M, Holtz W J, Prasad N, Lee S K, Keasling J D (2011b) BglBrick vectors and datasheets: a synthetic biology platform for gene expression. *J Biol Eng* 5:12).

In another aspect, the vector may further contain a BglII site and a BamHI site as restriction enzyme sites. In another aspect, the vector may further contain an EcoRI, a BglII site, a BamHI site and an XhoII site as restriction enzyme sites.

In another aspect, the shuttle vector for *Corynebacterium* and *E. coli* may further contain a target gene encoding a target protein desired to be overexpressed.

In another aspect, the shuttle vector for *Corynebacterium* and *E. coli* may contain two or more target genes.

In an aspect, the two or more target genes may be ones derived from different vectors. The different vectors may have a BglII site and a BamHI site on both sides of the target gene and the two target genes may be contained in one vector through complementary binding between the BglII site of one vector and the BamHI site of another vector.

BglBrick cloning is a cloning method which does not require a PCR amplification process. For example, target genes A and B respectively contained in two vectors can be simply cloned into one vector. Referring to FIG. 1, each vector has EcoRI site, BglII, BamHI and XhoI sites as restriction enzyme sites, which allows binding of partB immediately downstream of the target gene partA. It is possible because, upon enzyme treatment, the BamHI and the BglII sites can bind again with each other because their DNA strands are complementary to each other. In this manner, various genes can be simply cloned into one vector.

Figure 2:
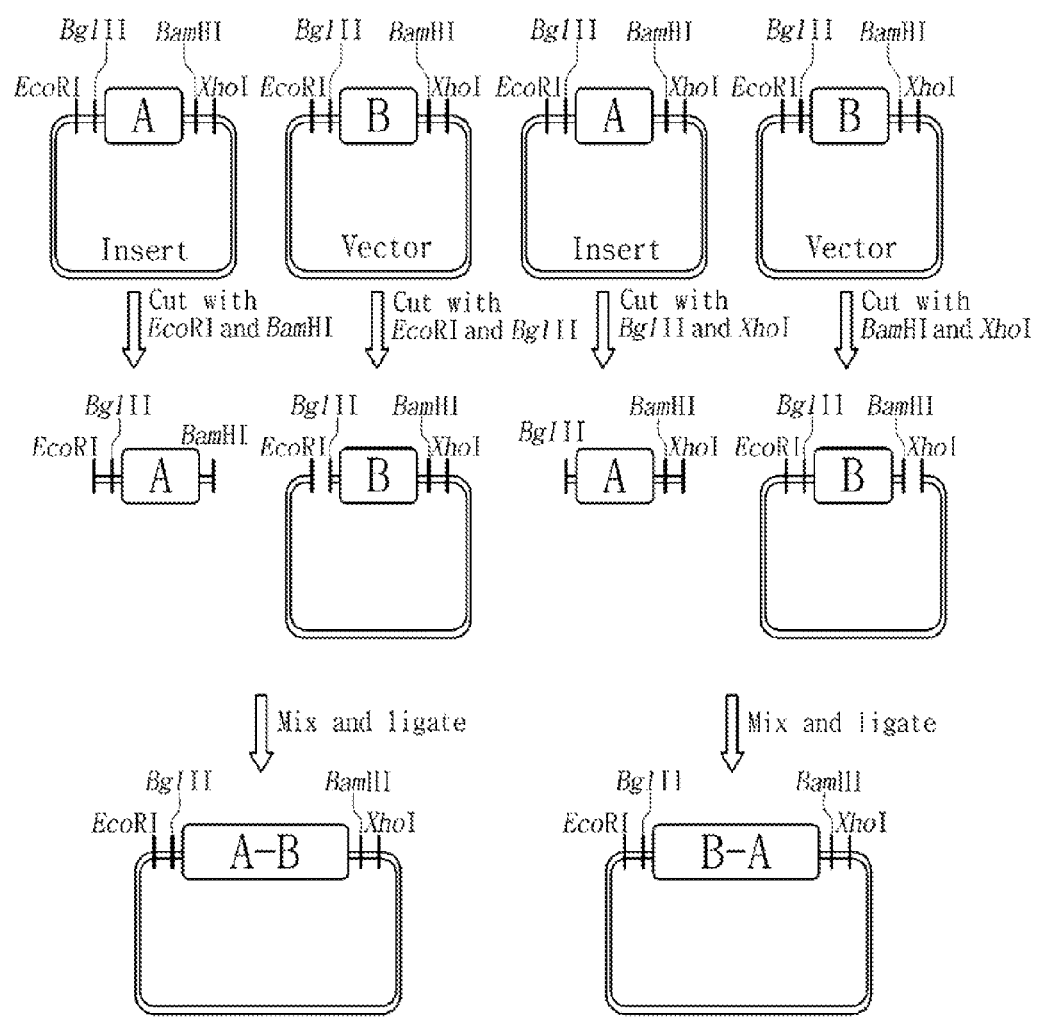
FIG. 2 schematically illustrates a procedure of obtaining a vector wherein target genes A-B and target genes B-A are inserted through BglBrick cloning.

In an aspect, the BglII site and the BamHI site may be located on both sides of the target gene. In another aspect, the order of the target gene and the restriction enzyme sites may be: EcoRI->BglII site->target gene->BamHI site->XhoII site. For example, let's call two vectors arranged in this order and having different target genes, i.e. a target gene A and a target gene B, a vector A and a vector B, respectively. By treating the vector A with restriction enzymes EcoRI and BamHI and treating the vector B with restriction enzymes EcoRI and BglII and then ligating the cut BglII site and the cut BamHI site through complementary binding, a shuttle vector in which the target genes A-B are inserted can be obtained (FIG. 2). Conversely, by treating the vector A with BglII and XhoI, and treating the vector B with BamHI and XhoI and then ligating, the target genes can be inserted in the order of B-A (FIG. 2).

In an aspect, the pBbEB1c-RFP shuttle vector may be a vector wherein a replication origin pBL1 derived from *Corynebacterium glutamicum* is inserted into a vector of SEQ ID NO 4 and the replication origin pBL1 may be located upstream of a replication origin ColE1 of *E. coli*.

For example, the shuttle vector according to the present disclosure may be a shuttle vector prepared newly using the BglBrick vectors published in the literature such as pBbE1c-RFP, pBbA2k-RFP and pBbE5c-RFP (Lee T S, Krupa R A, Zhang F, Hajimorad M, Holtz W J, Prasad N, Lee S K, Keasling J D (2011b) BglBrick vectors and datasheets: a synthetic biology platform for gene expression. *J Biol Eng* 5:12) and pXMJ19 (Jakoby M et al., (1999) "Construction and application of new *Corynebacterium glutamicum* vectors." *Biotechnology Techniques* 13, 437-441). The shuttle vector according to the present disclosure will be called a CoryneBrick vector. In an aspect, the CoryneBrick vector may be prepared by a CPEC cloning method or a traditional restriction-ligation cloning method. First, a pBbE1c-RFP vector may be prepared by inserting the *Corynebacterium glutamicum* replication origin pBL1 of a pXMJ19 vector into a specific portion using the CPEC method. For example, the vector may be a vector having a sequence of SEQ ID NO 1.

In SEQ ID NO 1, lacI is 76-1167, pTrc is 1224-1463 and pBL1 is 2477-5031.

In another aspect, the shuttle vector for *Corynebacterium* and *E. coli* may be a pBbEB2c-RFP vector containing a tetR repressor and a tetA promoter. In an aspect, the vector may be one prepared by removing a lacI repressor and a trc promoter from a vector of SEQ ID NO 1 using a restriction enzyme and inserting a tetR repressor and a tetA promoter. For example, the pBbEB2c-RFP vector may have a sequence of SEQ ID NO 2.

In SEQ ID NO 2, tetR is 21-627, tetA is 651-712 and pBL1 is 1885-4280.

In another aspect, the shuttle vector for *Corynebacterium* and *E. coli* may be a pBbEB5c-RFP vector containing a lacI repressor and a LacUV5 promoter. In an aspect, the vector may be one prepared by removing a lacI repressor and a trc promoter from a vector of SEQ ID NO 1 using a restriction enzyme, and inserting a lacI repressor and a LacUV5 promoter. For example, the pBbEB5c-RFP vector may have a sequence of SEQ ID NO 3.

In SEQ ID NO 3, lacI is 49-1140, LacUV5 is 1232-1585 and pBL1 is 2599-5153.

In an aspect, the present disclosure provides a host cell transformed with any of the above-described shuttle vectors. The host cell may be a *Corynebacterium* or *E. coli* cell. In an exemplary embodiment of the present disclosure, a *Corynebacterium glutamicum* strain may be used as a host cell to be transformed with the shuttle vector. *Corynebacterium glutamicum* is a bacterial strain producing various amino acids and nucleotides and is the most widely industrially used strain at present. The wild type is known to be capable of using glucose and sucrose as carbon sources, but not xylose and cellobiose or starch. A variety of amino acids and chemicals can be produced using the carbon sources that could not be used by *Corynebacterium glutamicum*, using a metabolic engineering technique.

In an aspect, the present disclosure provides a method for producing a substance, including culturing the transformed host cell described above. The method may produce two or more proteins at the same time. The produced two or more proteins may invoke a mechanism necessary for producing useful substances or the proteins themselves may be industrially useful. In an aspect, the substance may be an amino acid.

In an aspect, the present disclosure provides a method for preparing a multi-shuttle vector containing two or more target genes. For example, the method may include inserting a target gene into the shuttle vector according to an exemplary embodiment of the present disclosure, wherein the shuttle vector already contains one or more target gene before the insertion of the target gene, and the step of inserting includes forming complementary binding between the BglII site located upstream of the pre-existing target gene or the target gene to be inserted into the shuttle vector; and the BamHI site located downstream of the pre-existing target gene or another target gene to be inserted into the shuttle vector.

In an aspect, the complementary binding may be formed between the BglII site located upstream of the pre-existing target gene and the BamHI site located downstream of another target gene to be inserted into the shuttle vector, and, as a result of the complementary binding, the inserted target gene may be inserted upstream of the pre-existing target gene. For example, a procedure of inserting a target gene A to a shuttle vector already having a target gene B such that the genes are in the order of A-B is shown in the left side of FIG. 2. The target gene A to be inserted is designed such that it has EcoRI and BglII restriction enzyme sites at the upstream side, and a BamHI restriction enzyme site at the downstream side. This may be accomplished by using a vector having the target gene A, and having EcoRI and BglII restriction enzyme sites upstream thereof, and BamHI and XhoI restriction enzyme sites downstream thereof. By treating the vector with restriction enzymes EcoRI and BamHI, the target gene A having EcoRI and BglII restriction enzyme sites at the upstream side and a BamHI restriction enzyme site at the downstream side may be obtained. Meanwhile, a vector having the target gene B and having EcoRI and BglII restriction enzyme sites upstream of B, and BamHI and XhoI restriction enzyme sites downstream thereof is treated with restriction enzymes EcoRI and BglII. When the restriction enzyme site-containing and target A- and target B-containing vectors are mixed, complementary binding is formed between the BglII site located upstream of the target gene B of the vector and the BamHI site located downstream of the target gene A to be inserted into the shuttle vector and, as a result, a vector wherein the target genes are inserted in the order of A-B can be obtained.

In another aspect, the complementary binding may be formed between the BglII site located upstream of another target gene to be inserted into the shuttle vector and the BamHI site located downstream of the target gene of the shuttle vector, and, as a result of the complementary binding, the target gene may be inserted downstream of the pre-existing target gene. For example, a procedure of inserting a target gene A to a shuttle vector already having a target gene B such that the genes are in the order of B-A is shown in the right side of FIG. 2. The target gene A to be inserted is designed such that it has a BglII restriction enzyme site at the upstream side and BamHI and XhoI restriction enzyme sites at the downstream side. This may be accomplished by using a vector having the target gene A and having EcoRI and BglII restriction enzyme sites upstream of the A, and BamHI and XhoI restriction enzyme sites downstream of the A. By treating the vector with restriction enzymes BglII and XhoI, the target gene A having EcoRI and BglII restriction enzyme sites at the upstream side, and BamHI and XhoI restriction enzyme sites at the downstream side may be obtained. Meanwhile, a vector having the target gene B, and having EcoRI and BglII restriction enzyme sites upstream of B and BamHI and XhoI restriction enzyme sites downstream thereof is treated with restriction enzymes BamHI and XhoI. When the restriction enzyme site-containing and target A- and target B-containing vectors are mixed, complementary binding is formed between the BamHI site located downstream of the target gene B of the vector and the BglII site located upstream of the target gene A to be inserted into the shuttle vector and, as a result, a vector wherein the target genes are inserted in the order of B-A can be obtained.

In another aspect, the method may further include, before the step of inserting, preparing a restriction enzyme site-comprising target gene wherein the BglII site is located upstream of the target gene to be inserted and the BamHI site is located downstream of the target gene to be inserted. The restriction enzyme site-containing target gene may be prepared according to any method known in the art. For example, as described above, a vector having the target gene to be inserted and having EcoRI and BglII restriction enzyme sites upstream of the target and BamHI and XhoI restriction enzyme sites downstream thereof may be used.

Example 1

Construction of pBbEB1c-RFP as Novel CoryneBrick Vector

Figure 3:
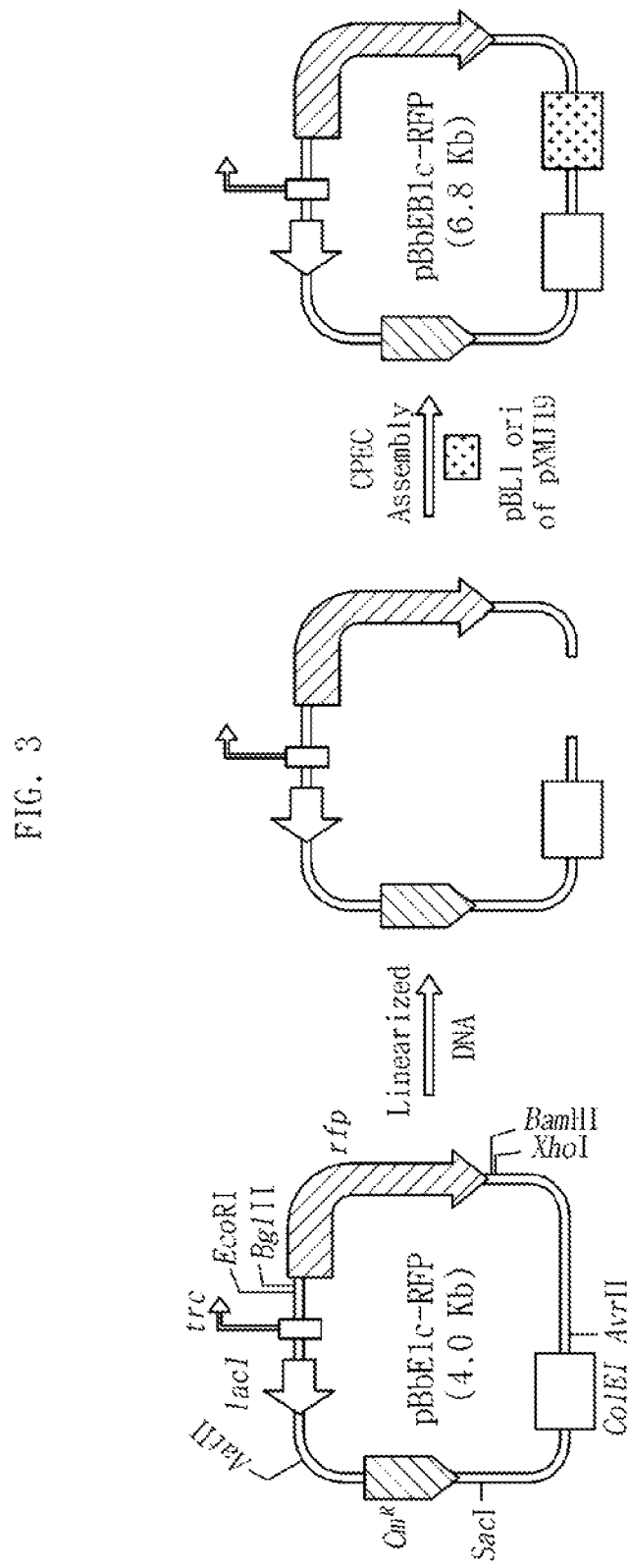
FIG. 3 schematically illustrates development of a pBbEB1c-RFP vector as one of CoryneBrick vectors using the CPEC method.

A BglBrick plasmid pBbE1c-RFP (Lee T S, Krupa R A, Zhang F, Hajimorad M, Holtz W J, Prasad N, Lee S K, Keasling J D (2011b) BglBrick vectors and datasheets: a synthetic biology platform for gene expression. *J Biol Eng* 5:12) and a pXMJ19 vector having a *C. glutamicum* replication origin pBL1 (Jakoby M et al., (1999) "Construction and application of new *Corynebacterium glutamicum* vectors." *Biotechnology Techniques* 13, 437-441) were used as DNA templates for construction of a CoryneBrick vector pBbEB1c-RFP. The *C. glutamicum* replication origin pBL1 of the pXMJ19 was assembled into the pBbE1c-RFP using the CPEC method (Quan J, Tian J (2009) Circular Polymerase Extension Cloning of Complex Gene Libraries and Pathways. *PLoS ONE* 4(7): e6441. doi:10.1371/journal.pone.0006441). The resulting vector was transformed into *E. coli* HIT-DH5α (Cat# RH617-J80, RBC Bioscience) and then extracted with mini-prep. Since the assembled vector had the possibility of mutation because it was prepared through PCR, the entire sequence was identified by plasmid sequencing. Thus obtained CoryneBrick vector was named as pBbEB1c-RFP (FIG. 3).

Example 2

Figure 4:
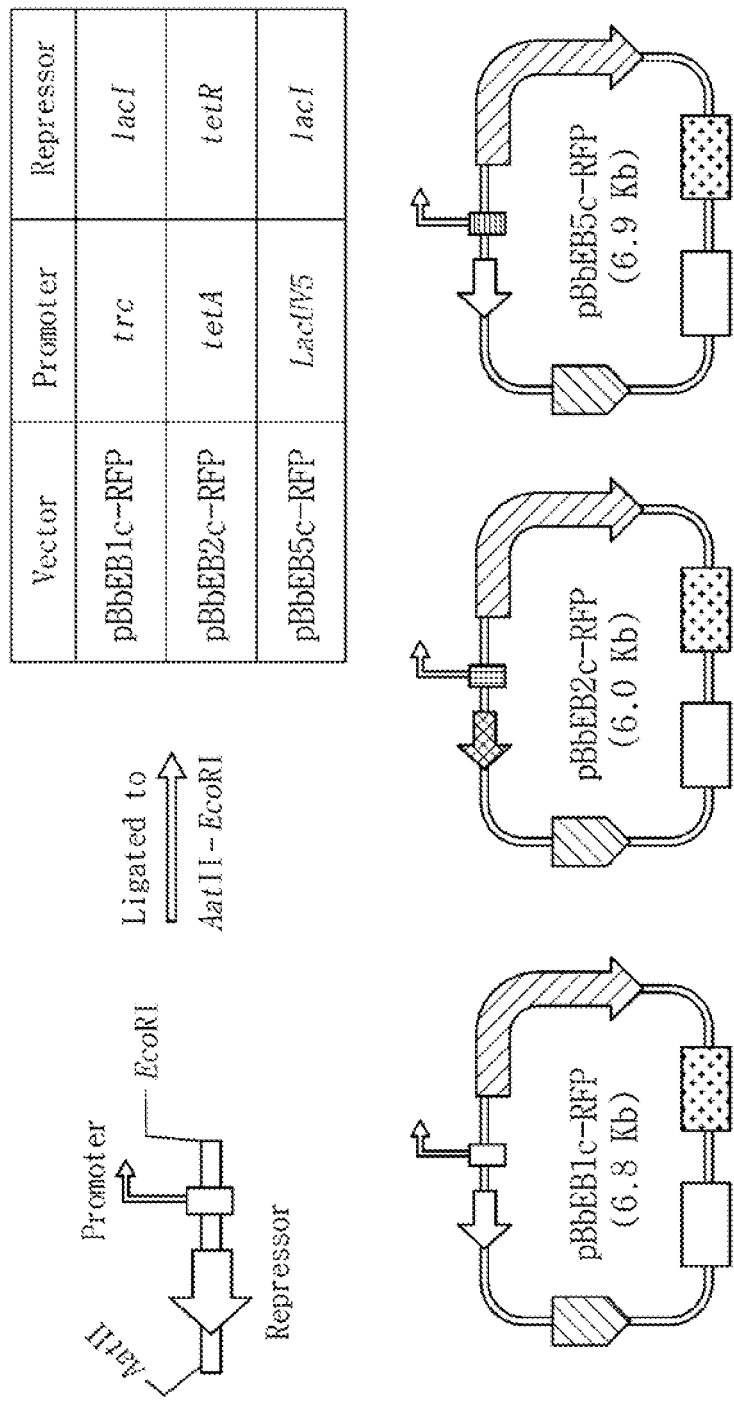
FIG. 4 illustrates assembly of pBbEB2c-RFP and pBbEB5c-RFP vectors as CoryneBrick vectors through restriction enzyme treatment and ligation.

Construction of pBbEB2c-RFP and pBbEB5c-RFP Using pBbEB1c-RFP CoryneBrick Vector The pBbEB1c-RFP prepared in Example 1 and the previously known pBbA2k-RFP (Lee T S, Krupa R A, Zhang F, Hajimorad M, Holtz W J, Prasad N, Lee S K, Keasling J D (2011b) BglBrick vectors and datasheets: a synthetic biology platform for gene expression. *J Biol Eng* 5:12) and pBbE5c-RFP (Lee T S, Krupa R A, Zhang F, Hajimorad M, Holtz W J, Prasad N, Lee S K, Keasling J D (2011b) BglBrick vectors and datasheets: a synthetic biology platform for gene expression. *J Biol Eng* 5:12) were used to prepare CoryneBrick vectors pBbEB2c-RFP and pBbEB5c-RFP. Because only the promoter and repressor portions of pBbA2k-RFP and pBbE5c-RFP were necessary, instead of using the CPEC method as in Example 1, the promoter and repressor sites of the pBbEB1c-RFP prepared in Example 1 were removed with restriction enzymes and the promoter and repressor portions of pBbA2k-RFP and pBbE5c-RFP were inserted there. The used restriction enzymes were AatII and EcoRI. The promoter and repressor portions of pBbA2k-RFP and pBbE5c-RFP and the promoter and repressor portions of pBbEB1c-RFP were cut using the restriction enzymes and then the promoter and repressor portions of pBbA2k-RFP and pBbE5c-RFP were inserted into the restriction enzyme-treated pBbEB1c-RFP to prepare pBbEB2c-RFP and pBbEB5c-RFP, respectively (FIG. 4).

Example 3

Testing of CoryneBrick Vector for Gene Expression in *C. glutamicum*

It was tested whether the three CoryneBrick vectors prepared in Examples 1 and 2 are suitable for gene expression in *C. glutamicum*. The expression kinetics of the red fluorescent protein (RFP) inserted in each vector was analyzed. For the analysis, excitation and emission at wavelengths of 535 nm and 620 nm, respectively, were measured using an automatic microplate reader (Tecan Infinite M200 pro, Tecan Group Ltd., Switzerland). Specific fluorescence (fluorescence intensity/cell density) during the growth of the strain was measured using the instrument. After transformation of pBbEB1c-RFP, pBbEB2c-RFP and pBbEB5c-RFP into the *Corynebacterium glutamicum* strain (ATCC 13032), the transformed cells were cultured overnight in BHIS (brain-heart infusion, supplemented) medium at 30° C. The cultured cells were cultured in fresh BHIS medium for 4 hours using 1 mM IPTG (pBbEB1c-RFP, pBbEB5c-RFP) or 100 nM aTc (pBbEB2c-RFP) as an inducer with a start OD of 0.1. 200 μL of the culture was transferred onto a 96-well plate and fluorescence intensity and optical density were measured at 30° C. and 200 rpm for 50 hours. The result is shown in FIG. 5.

Figure 5:
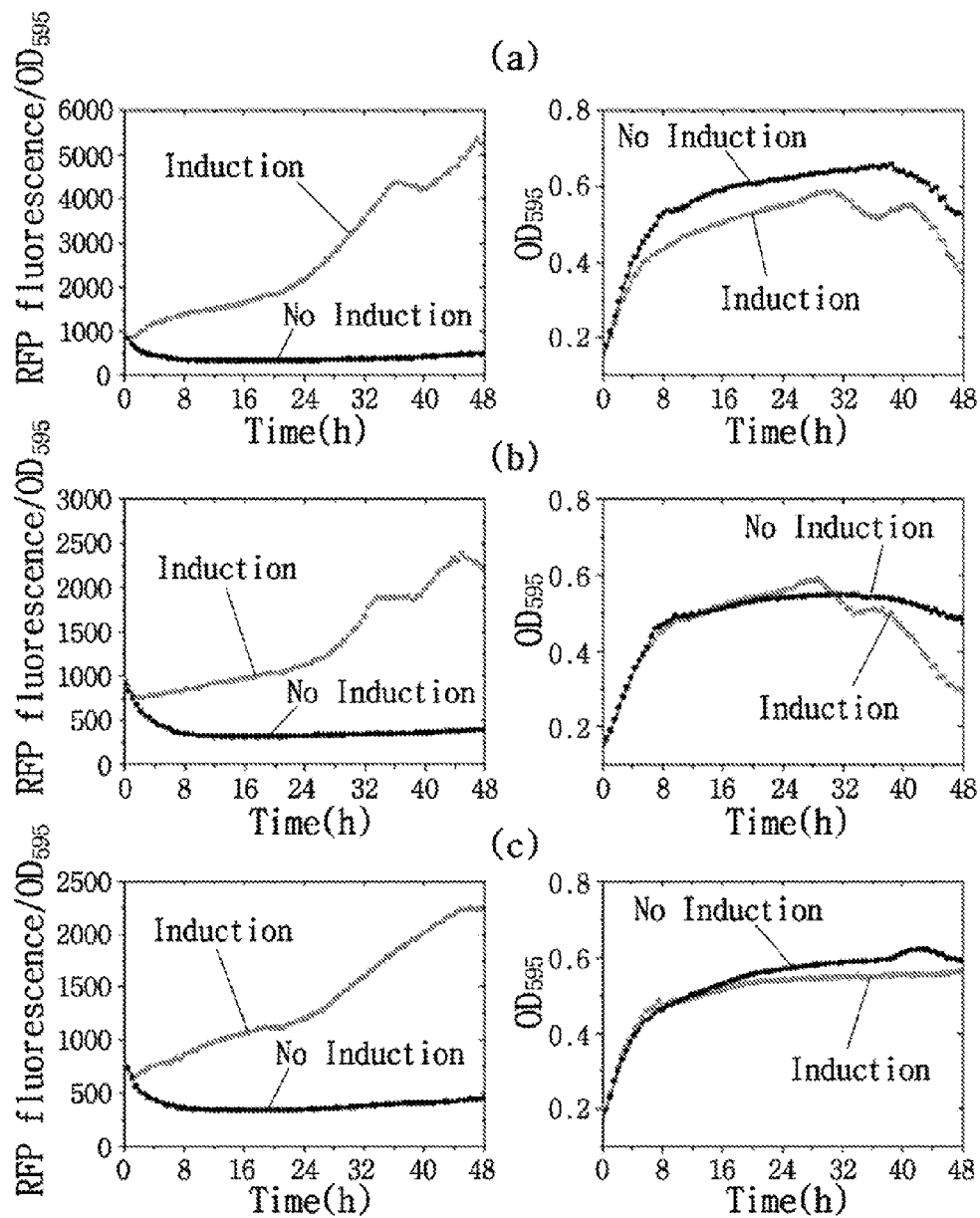
FIG. 5 shows a result of measuring RFP-specific fluorescence and growth of *C. glutamicum* strains transformed with three CoryneBrick vectors (a. pBbEB1c-RFP, b. pBbEB2c-RFP, c. pBbEB5c-RFP) (IPTG or aTc induction; no induction).

FIG. 5 shows the RFP-specific fluorescence and growth of the *C. glutamicum* strain transformed with the three CoryneBrick vectors (a. pBbEB1c-RFP, b. pBbEB2c-RFP, c. pBbEB5c-RFP) (red: IPTG or aTc induction, black: no induction). As seen from a and c in FIG. 5, the pBbEB1c-RFP and the pBbEB5c-RFP induced with 1 mM IPTG exhibited 5-fold and 2.5-fold increased specific fluorescence in 48 hours as compared to the non-induced control. The cells not induced with IPTG maintained a constant value. From this result, it was confirmed that the pBbEB1c-RFP having the trc promoter exhibits about 2-fold stronger RFP gene expression as compared to the pBbEB5c-RFP having the lacUV5 promoter. Similarly to the pBbEB5c-RFP, the pBbEB2c-RFP having the tetA promoter and the tetR repressor exhibited about 2.5-fold stronger specific fluorescence when induced with 100 nm aTc as compared to the non-induced cells.

From this result, it was confirmed that the pBbEB1c having the trc promoter exhibits about 2-fold stronger gene expression as compared to the pBbEB5c having the lacUV5 promoter or the pBbEB2c having the tetA promoter.

Example 4

Culturing of *C. glutamicum* Strain Wherein pBbEB1c-xylA, pBbEB1c-xylA-xylB and pBbEB1c-xylB-xylA are Introduced in Medium Containing 1% Xylose After the operation of the CoryneBrick vectors in *C. glutamicum* was confirmed, codons were optimized using the Gene Designer 2.0 software (DNA2.0, MenloPark, CA, USA). *E. coli* xylA (xylose isomerase) and xylB (xylulokinase) genes prepared by the BglBrick method were inserted into the pBbEB1c-RFP vector and it was investigated whether xylose was consumed. It was because, although the wild-type *C. glutamicum* strain is presumed to have the xylB gene for metabolizing xylose, it cannot use xylose as a carbon source because it lacks the xylA gene. Since it is already known that *C. glutamicum* to which xylA and xylB have been introduced can consume xylose, if the *Corynebacterium glutamicum* could consume xylose, it directly confirms that the CoryneBrick vector constructed according to the present disclosure operates normally.

The *C. glutamicum* strain was transformed with codon-optimized *E. coli* xylA and xylB using the CoryneBrick vector. The codon-optimized *E. coli* xylA and xylB genes were acquired from GenScript, and EcoRI and BglII sites were attached upstream of the gene and a BamHI site was attached downstream of the gene for use in BglBrick cloning. First, the xylA gene was inserted into the pBbEB1c vector using restriction enzymes EcoRI and BamHI. The resulting pBbEB1c-xylA was transformed into *Corynebacterium glutamicum* (CgEcXylA) and cultured for 56 hours in CGXII medium+1% xylose medium at 30° C. and 200 rpm, with a start OD of 1. The specific growth rate was 0.09/h and the final OD was about 15.7.

Then, the codon-optimized xylB gene was inserted upstream or downstream of xylA by the BglBrick method. After transformation, *Corynebacterium glutamicum* was cultured in the presence of 1% xylose. To prepare pBbEB1c-xylA-xylB, the pBbEB1c-xylA was treated with BamHI and XhoI restriction enzymes and the xylB gene was ligated after treating with BglII and XhoI restriction enzymes. To prepare pBbEB1c-xylB-xylA, the pBbEB1c-xylA was treated with EcoRI and BglII restriction enzymes and xylB was ligated after treating with EcoRI and BamHI restriction enzymes. After the culturing, the *Corynebacterium glutamicum* transformed with the pBbEB1c-xylA-xylB (CgEcXylAB) showed a specific growth rate of 0.11/h, which is slightly faster than that for CgEcXylA, and a final OD, which is similar to that for CgEcXylA. The *Corynebacterium glutamicum* transformed with the pBbEB1c-xylB-xylA (CgEcXylBA) showed no significant difference in specific growth rate and final OD as compared to CgEcXylA (see FIG. 6).

Figure 6:
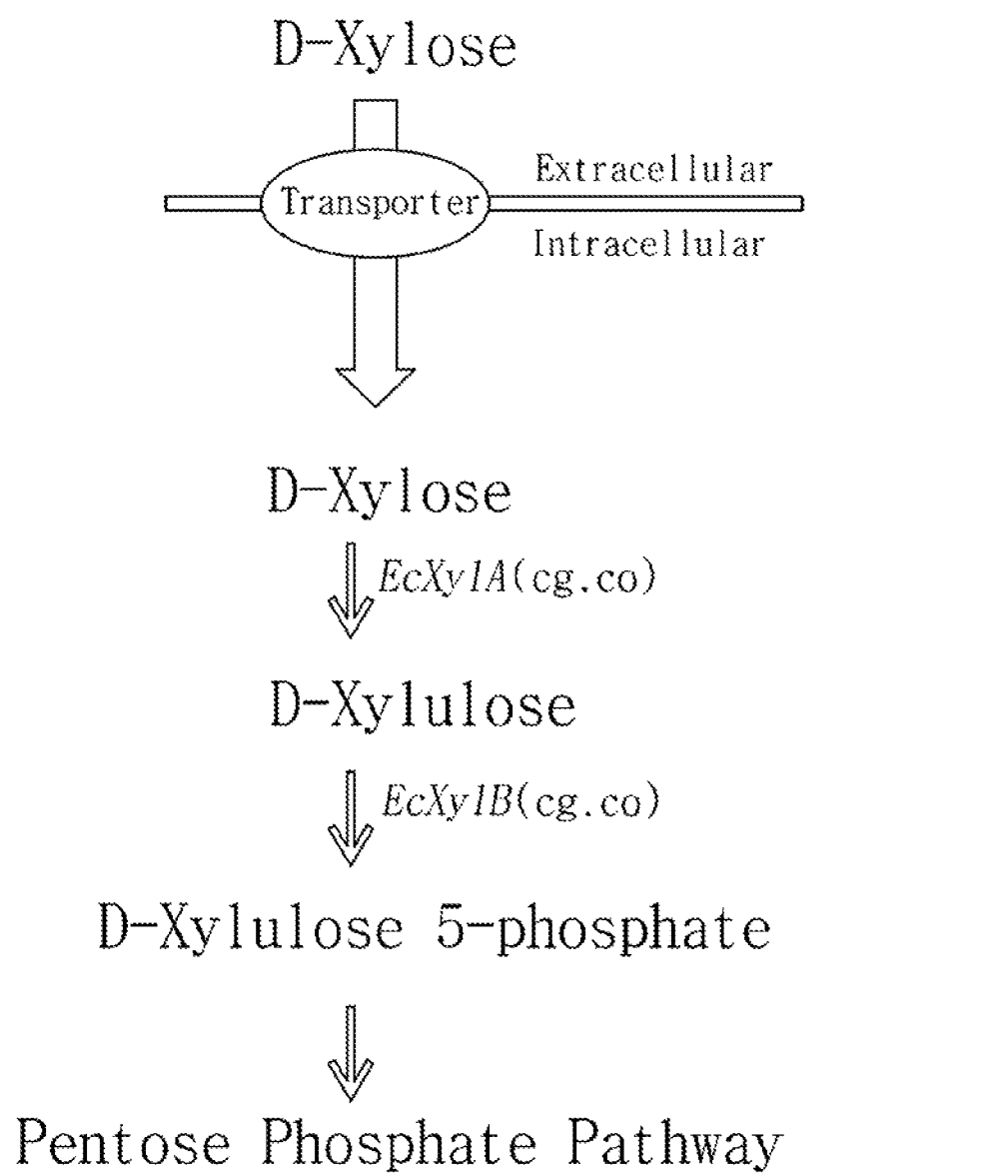
FIG. 6 illustrates a metabolic pathway of xylose.
Figure 7:
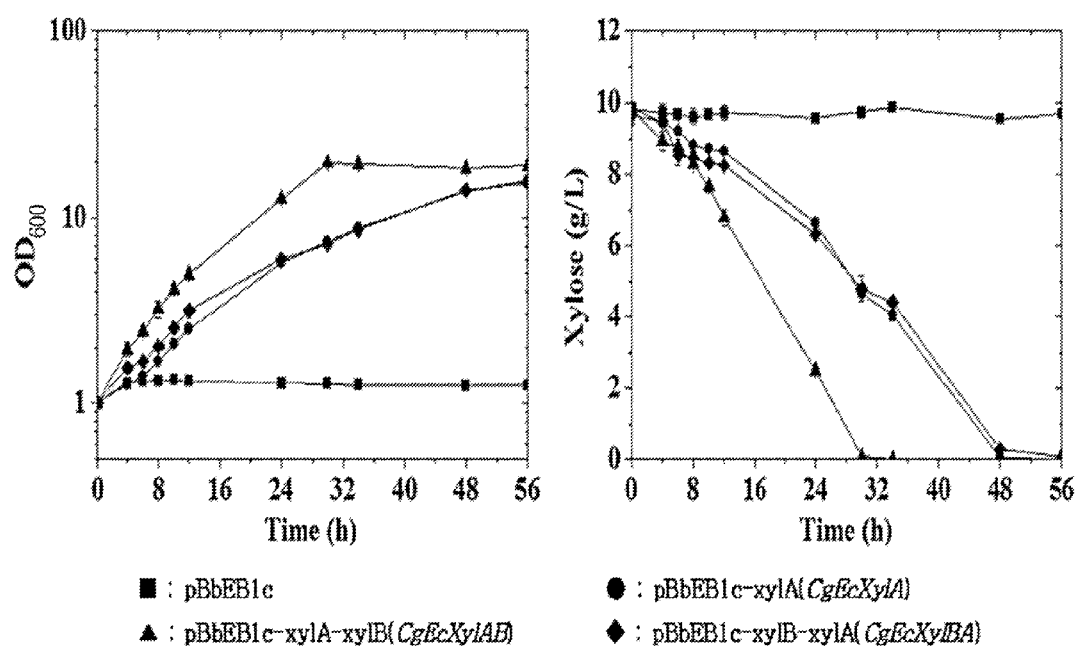
FIG. 7 shows growth of *Corynebacterium glutamicum* in which the target genes xylA and xylB are introduced and xylose concentrations in a medium containing 1% xylose.
Figure 8:
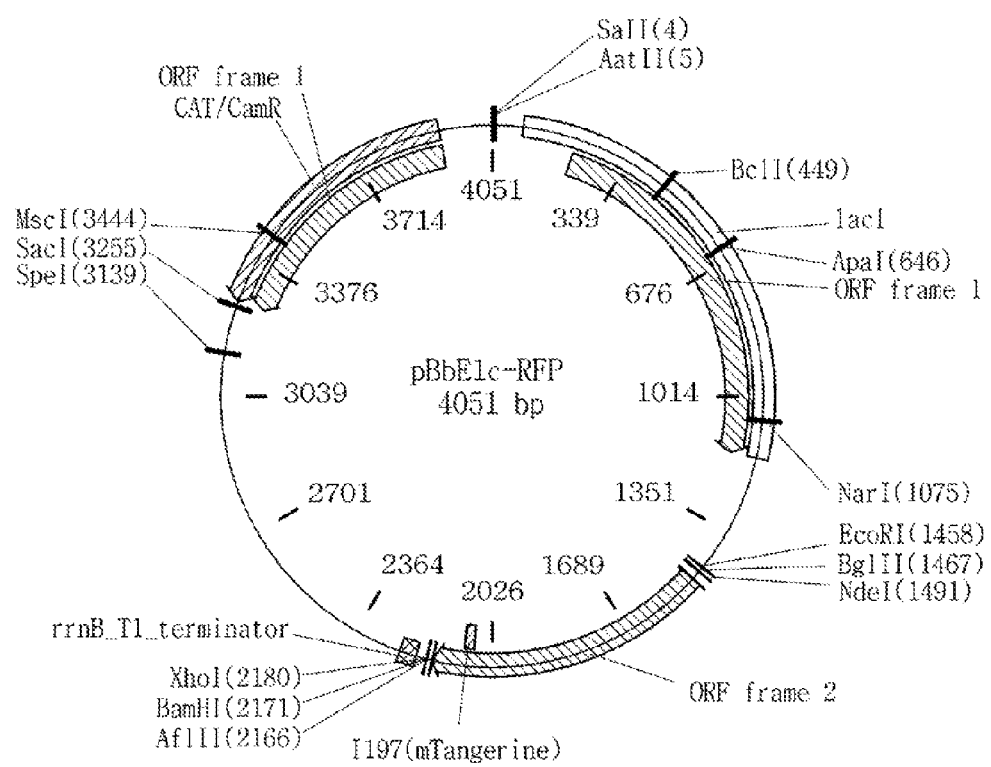
FIG. 8 shows a map of a pBbE1c-RFP vector as a template for constructing a vector according to an exemplary embodiment of the present disclosure.

Xylose consumption of each strain was analyzed by HPLC after sampling the culture every hour and centrifuging the sample at 14000 rpm for 10 minutes. The result is shown in FIG. 6.

SEQ ID NO 4: pBbE1c-RFP (4051 bps)

```
gacgtcgacaccatcgaatggtgcaaaacctttcg
cggtatggcatgatagcgcccggaagagagtcaat
tcagggtggtgaatgtgaaaccagtaacgttatac
gatgtcgcagagtatgccggtgtctcttatcagac
cgtttcccgcgtggtgaaccaggccagccacgttt
ctgcgaaaacgcgggaaaaagtggaagcggcgatg
gcggagctgaattacattcccaaccgcgtggcaca
acaactggcgggcaaacagtcgttgctgattggcg
ttgccacctccagtctggccctgcacgcgccgtcg
caaattgtcgcggcgattaaatctcgcgccgatca
actgggtgccagcgtggtggtgtcgatggtagaac
gaagcggcgtcgaagcctgtaaagcggcggtgcac
aatcttctcgcgcaacgcgtcagtgggctgatcat
taactatccgctggatgaccaggatgccattgctg
tggaagctgcctgcactaatgttccggcgttattt
cttgatgtctctgaccagacacccatcaacagtat
tattttctcccatgaagacggtacgcgactgggcg
tggagcatctggtcgcattgggtcaccagcaaatc
gcgctgttagcgggcccattaagttctgtctcggc
gcgtctgcgtctggctggctggcataaatatctca
ctcgcaatcaaattcagccgatagcggaacgggaa
ggcgactggagtgccatgtccggttttcaacaaac
catgcaaatgctgaatgagggcatcgttcccactg
cgatgctggttgccaacgatcagatggcgctgggc
gcaatgcgcgccattaccgagtccgggctgcgcgt
tggtgcggatatctcggtagtgggatacgacgata
ccgaagacagctcatgttatatcccgccgttaacc
accatcaaacaggattttcgcctgctggggcaaac
cagcgtggaccgcttgctgcaactctctcagggcc
aggcggtgaagggcaatcagctgttgcccgtctca
ctggtgaaaagaaaaaccaccctggcgcccaatac
gcaaaccgcctctccccgcgcgttggccgattcat
taatgcagctggcacgacaggtttcccgactggaa
agcgggcagtgagcgcaacgcaattaatgtaagtt
agcgcgaattgatctggtttgacagcttatcatcg
actgcacggtgcaccaatgcttctggcgtcaggca
gccatcggaagctgtggtatggctgtgcaggtcgt
aaatcactgcataattcgtgtcgctcaaggcgcac
tcccgttctggataatgttttttgcgccgacatca
taacggttctggcaaatattctgaaatgagctgtt
gacaattaatcatccggctcgtataatgtgtggaa
ttgtgagcggataacaatttcagaattcaaaagat
cttttaagaaggagatatacatatggcgagtagcg
aagacgttatcaaagagttcatgcgtttcaaagtt
cgtatggaaggttccgttaacggtcacgagttcga
aatcgaaggtgaaggtgaaggtcgtccgtacgaag
gtacccagaccgctaaactgaaagttaccaaaggt
ggtccgctgccgttcgcttgggacatcctgtcccc
gcagttccagtacggttccaaagcttacgttaaac
acccggctgacatcccggactacctgaaactgtcc
ttcccggaaggtttcaaatgggaacgtgttatgaa
cttcgaagacggtggtgttgttaccgttacccagg
actcctccctgcaagacggtgagttcatctacaaa
gttaaactgcgtggtaccaacttcccgtccgacgg
tccggttatgcagaaaaaaaccatgggttgggaag
cttccaccgaacgtatgtacccggaagacggtgct
ctgaaaggtgaaatcaaaatgcgtctgaaactgaa
agacggtggtcactacgacgctgaagttaaaacca
cctacatggctaaaaaaccggttcagctgccgggt
gcttacaaaaccgacatcaaactggacatcacctc
``` ccacaacgaagactacaccatcgttgaacagtacg aacgtgctgaaggtcgtcactccaccggtgcttaa ggatccaaactcgagtaaggatctccaggcatcaa ataaaacgaaaggctcagtcgaaagactgggcctt tcgttttatctgttgtttgtcggtgaacgctctct actagagtcacactggctcaccttcgggtgggcct ttctgcgtttatacctagggcgttcggctgcggcg agcggtatcagctcactcaaaggcggtaatacggt tatccacagaatcaggggataacgcaggaaagaac atgtgagcaaaaggccagcaaaaggccaggaaccg taaaaaggccgcgttgctggcgttttttccataggc tccgcccccctgacgagcatcacaaaaatcgacgc tcaagtcagaggtggcgaaacccgacaggactata aagataccaggcgtttccccctggaagctccctcg tgcgctctcctgttccgaccctgccgcttaccgga tacctgtccgcctttctcccttcgggaagcgtggc gctttctcatagctcacgctgtaggtatctcagtt cggtgtaggtcgttcgctccaagctgggctgtgtg cacgaaccccccgttcagcccgaccgctgcgcctt atccggtaactatcgtcttgagtccaacccggtaa gacacgacttatcgccactggcagcagccactggt aacaggattagcagagcgaggtatgtaggcggtgc tacagagttcttgaagtggtggcctaactacggct acactagaaggacagtatttggtatctgcgctctg ctgaagccagttaccttcggaaaaagagttggtag ctcttgatccggcaaacaaaccaccgctggtagcg gtggtttttttgtttgcaagcagcagattacgcgc agaaaaaaaggatctcaagaagatcctttgatctt ttctacggggtctgacgctcagtggaacgaaaact cacgttaagggattttggtcatgactagtgcttgg attctcaccaataaaaaacgcccggcggcaaccga gcgttctgaacaaatccagatggagttctgaggtc attactggatctatcaacaggagtccaagcgagct cgatatcaaattacgccccgccctgccactcatcg cagtactgttgtaattcattaagcattctgccgac atggaagccatcacaaacggcatgatgaacctgaa tcgccagcggcatcagcaccttgtcgccttgcgta taatatttgcccatggtgaaaacggggggcgaagaa gttgtccatattggccacgtttaaatcaaaactgg tgaaactcacccaggattggctgagacgaaaaac atattctcaataaacccctttagggaaataggccag gttttcaccgtaacacgccacatcttgcgaatata tgtgtagaaactgccggaaatcgtcgtggtattca ctccagagcgatgaaaacgtttcagtttgctcatg gaaaacggtgtaacaagggtgaacactatcccata tcaccagctcaccgtctttcattgccatacgaaat tccggatgagcattcatcaggcgggcaagaatgtg aataaaggccggataaaaacttgtgcttatttttct ttacggtctttaaaaaggccgtaatatccagctga acggtctggttataggtacattgagcaactgactg aaatgcctcaaaatgttctttacgatgccattggg atatatcaacggtggtatatccagtgatttttttc tccattttagcttccttagctcctgaaaatctcga taactcaaaaaatacgcccggtagtgatcttattt cattatggtgaaagttggaacctcttacgtgccga tcaacgtctcattttcgccagatatc

---

What is claimed is:

1. A shuttle vector for *Corynebacterium glutamicum* and *E. coli*, comprising:
   a repressor selected from a group consisting of a lacI repressor and a tetR repressor;
   a promoter selected from a group consisting of a trc promoter, a tetA promoter and a LacUV5 promoter; a replication origin pBL1 derived from *Corynebacterium glutamicum*; and a replication origin ColE1 of *E. coli*, wherein the vector is
   a pBbEB1c vector comprising a replication origin pBL1, a replication origin ColE1, a lacI repressor and a trc promoter;
   a pBbEB2c vector comprising a replication origin pBL1, a replication origin ColE1, a tetR repressor and a tetA promoter; or
   a pBbEB5c vector comprising a replication origin pBL1, a replication origin ColE1, a lacI repressor and a LacUV5 promoter.

2. The shuttle vector for *Corynebacterium glutamicum* and *E. coli* according to claim 1, wherein the vector further comprises a chloramphenicol-resistant reporter gene.

3. The shuttle vector for *Corynebacterium glutamicum* and *E. coli* according to claim 1, wherein the vector further comprises a red fluorescent protein (RFP) gene.

4. The shuttle vector for *Corynebacterium glutamicum* and *E. coli* according to claim 1, wherein the vector further comprises a BglII site and a BamHI site as restriction enzyme sites.

5. The shuttle vector for *Corynebacterium glutamicum* and *E. coli* according to claim 4, wherein the shuttle vector for *Corynebacterium glutamicum* and *E. coli* further comprises a target gene encoding a target protein desired to be overexpressed.

6. The shuttle vector for *Corynebacterium glutamicum* and *E. coli* according to claim 5, wherein the BglII site and the BamHI site are located on both sides of the target gene.

7. The shuttle vector for *Corynebacterium glutamicum* and *E. coli* according to claim 6, wherein the shuttle vector for *Corynebacterium glutamicum* and *E. coli* comprises two or more target genes.

8. The shuttle vector for *Corynebacterium glutamicum* and *E. coli* according to claim 7, wherein the two or more target genes are comprised in one vector through complementary binding between the BglII site located upstream of one target gene and the BamHI site located downstream of another target gene.

9. The shuttle vector for *Corynebacterium glutamicum* and *E. coli* according to claim 1, wherein the vector is a pBbEB1c-RFP vector.

10. The shuttle vector for *Corynebacterium glutamicum* and *E. coli* according to claim 1, wherein the shuttle vector is a vector wherein a replication origin pBL1 derived from *Corynebacterium glutamicum* is inserted into a vector of SEQ ID NO 4 and the replication origin pBL1 is located upstream of a replication origin ColE1 of *E. coli* provided that an RFP sequence in the pBbEB1c-RFP vector may be deleted or replaced with a different sequence.

11. The shuttle vector for *Corynebacterium glutamicum* and *E. coli* according to claim 1, wherein the vector has a sequence of SEQ ID NO 1 provided that an RFP sequence in the pBbEB1c-RFP vector may be deleted or replaced with a different sequence.

12. The shuttle vector for *Corynebacterium glutamicum* and *E. coli* according to claim 1, wherein the vector is a pBbEB2c-RFP vector.

13. The shuttle vector for *Corynebacterium glutamicum* and *E. coli* according to claim 1, wherein the vector is one prepared by removing a lacI repressor and a trc promoter from a vector of SEQ ID NO 1 using a restriction enzyme and inserting a tetR repressor and a tetA promoter provided that an RFP sequence in the pBbEB2c-RFP vector may be deleted or replaced with a different sequence.

14. The shuttle vector for *Corynebacterium glutamicum* and *E. coli* according to claim 1, wherein the vector has a sequence of SEQ ID NO 2 provided that an RFP sequence in the pBbEB2c-RFP vector may be deleted or replaced with a different sequence.

15. The shuttle vector for *Corynebacterium glutamicum* and *E. coli* according to claim 1, wherein the vector is a pBbEB5c-RFP vector.

16. The shuttle vector for *Corynebacterium glutamicum* and *E. coli* according to claim 1, wherein the vector is one prepared by removing a lacI repressor and a trc promoter from a vector of SEQ ID NO 1 using a restriction enzyme and inserting a lacI repressor and a LacUV5 promoter provided that an RFP sequence in the pBbEB5c-RFP vector may be deleted or replaced with a different sequence.

17. The shuttle vector for *Corynebacterium glutamicum* and *E. coli* according to claim 1, wherein the vector has a sequence of SEQ ID NO 3 provided that an RFP sequence in the pBbEB5c-RFP vector may be deleted or replaced with a different sequence.

18. A host cell transformed with the shuttle vector according to claim 1.

19. The host cell according to claim 18, wherein the host cell is a *Corynebacterium glutamicum* or *E. coli*.

20. The host cell according to claim 19, wherein the host cell is a *Corynebacterium glutamicum*.

* * * * *